(12) United States Patent
Talton et al.

(10) Patent No.: US 12,723,026 B2
(45) Date of Patent: Sep. 1, 2026

(54) COMPOSITIONS AND METHODS FOR ORAL DELIVERY OF CRYSTALLINE TRIAPINE

(71) Applicant: NANOPHARMACEUTICS, INC., Alachua, FL (US)

(72) Inventors: James David Talton, Alachua, FL (US); Mianji Zhang, Alachua, FL (US); Otto Joseph Geoffroy, Alachua, FL (US); Lianhao Zhang, Alachua, FL (US)

(73) Assignee: Nanopharmaceutics, Inc., Alachua, FL (US)

( * ) Notice: Subject to any disclaimer, the term of this patent is extended or adjusted under 35 U.S.C. 154(b) by 0 days.

(21) Appl. No.: 19/540,272

(22) Filed: Feb. 13, 2026

(65) Prior Publication Data

US 2026/0184682 A1 Jul. 2, 2026

Related U.S. Application Data

(63) Continuation of application No. 19/326,396, filed on Sep. 11, 2025, now abandoned.

(60) Provisional application No. 63/739,512, filed on Dec. 28, 2024.

(51) Int. Cl.

| | |
|---|---|
| ***C07D 213/73*** | (2006.01) |
| ***A61K 9/16*** | (2006.01) |
| ***A61K 31/44*** | (2006.01) |

(52) U.S. Cl.

CPC .......... *C07D 213/73* (2013.01); *A61K 9/1611* (2013.01); *A61K 9/1617* (2013.01); *A61K 9/1623* (2013.01); *A61K 9/1635* (2013.01); *A61K 9/1652* (2013.01); *A61K 9/1694* (2013.01); *A61K 31/44* (2013.01)

(58) Field of Classification Search

CPC .. C07D 213/73; A61K 9/1611; A61K 9/1617; A61K 31/44; A61K 9/1635; A61K 9/1652; A61K 9/1694; A61K 9/1623

See application file for complete search history.

(56) References Cited

U.S. PATENT DOCUMENTS

| | | |
|---|---|---|
| 5,869,676 A | 2/1999 | Niu et al. |
| 2015/0250776 A1 | 9/2015 | Talton et al. |

OTHER PUBLICATIONS

Sudha R. Vippagunta, et al., Crystalline Solids, 48 Adv. Drug Del. Rev. 3 (Year: 2001).*

Christian R. Kowol, et al, Impact of Metal Coordination on Cytotoxicity of 3-Aminopyridine-2-carboxaldehyde Thiosemicarbazone (Triapine) and Novel Insights into Terminal Dimethylation, 52 J Med. Chem. 5032 (Year: 2009).*

Liu, Mao-Chi et al., "Synthesis and Antitumor Activity of Amino Derivatives of Pyridine-2-Carboxaldehyde Thiosemicarbazone", Journal of Medicinal Chemistry, vol. 35, No. 20, (Apr. 21, 1992), pp. 3672-3677.

Kowol, C. R. et al., "Impact of Metal Coordination on Cytotoxicity of 3-Aminopyridine-2-carboxaldehyde Thiosemicarbazone (Triapine) and Novel Insights into Terminal Dimethylation", Journal of Medicinal Chemistry, vol. 52, No. 16, (Jul. 28, 2009), pp. 5032-5043.

Plamthottam, S. et al., "Activity and electrochemical properties: iron complexes of the anticancer drug triapine and its analogs", Journal of Biological Inorganic Chemistry, vol. 24, (Jun. 27, 2019), pp. 621-632.

Taylor, S. E. et al., "Dose finding, bioavailability, and PK-PD of oral triapine and with concurrentchemoradiation for locally advanced cervical cancer and vaginal cancer (ETCTN 9892)", Cancer and Chemotherapy and Pharmacology, vol. 95, No. 4, (2025) (published Dec. 14, 2024), 12 pages.

* cited by examiner

*Primary Examiner* — Sean M Basquill

(74) *Attorney, Agent, or Firm* — Finnegan, Henderson, Farabow, Garrett & Dunner LLP

(57) ABSTRACT

The present disclosure addresses this need by providing crystalline fine particle forms of 3-AP, methods for preparation and the treatment for solid tumors and hematological malignancies. In certain aspects, the present disclosure provides novel methods of preparing the compound of Formula I thereof, or 3-APs, crystalline fine particle forms of 3-AP, and compositions comprising them. In certain aspects, the present disclosure provides novel crystalline fine particle form of 3-AP which may provide advantages including improved bioavailability and stability relative to other crystalline or amorphous forms. In other aspects, the present disclosure provides oral dosage forms of crystalline fine particle form of 3-AP and excipients with improved stability. In additional aspects, the present disclosure provides novel methods of synthesizing novel crystalline fine particle form of 3-AP, preparing crystalline 3-AP particle delivery systems (PDS), and preparing novel final dosage forms (FDF) of crystalline fine particle 3-AP. In certain aspects, the present disclosure provides novel crystalline forms of fine particle 3-AP which may provide advantages including improved bioavailability and stability relative to other crystalline or amorphous forms.

28 Claims, 10 Drawing Sheets

Formula I: ##STR00001##

Formula II: ##STR00002##

Formula III: ##STR00003##

Formula IV: ##STR00004##

1 2 3

3 4 5

5 6 7

3-AP (Mass 195.2)

Formula III (Mass 180.2)

Formula IV (Mass 446.3)

Formula II (Mass 212.3)

A

Example 2

B

Example 2

A

B

A

B

A

Example 3

B

COMPOSITIONS AND METHODS FOR ORAL DELIVERY OF CRYSTALLINE TRIAPINE

CROSS-REFERENCE TO RELATED APPLICATIONS

This application is a continuation of U.S. patent application Ser. No. 19/326,396, filed Sep. 11, 2025, which claims the benefit of priority of U.S. Provisional Patent Application No. 63/739,512 filed Dec. 28, 2024, both of which are incorporated herein by reference in their entirety.

FIELD OF THE DISCLOSURE

The present disclosure relates generally to a novel crystalline fine particle form of Triapine, particle delivery systems of the crystalline compound, methods of preparing such compositions, and therapeutic uses thereof. The compositions and methods described herein allow the novel crystalline fine particle form of Triapine to be administered by routes that are non-invasive to patients, such as by oral administration.

BACKGROUND

The compound of the present disclosure, Triapine, also known as 3-AP, a compound of Formula I: ##STR00001 ##, also referred to as 3-aminopyridine-2-carboxaldehyde thiosemicarbazone and (2E)-2-[(3-aminopyridin-2-yl)methylidene]hydrazine-1-carbothioamide, was originally described in Liu, et al., "Synthesis and Antitumor Activity of Amino Derivatives of Pyridine-2-carboxaldehyde Thiosemicarbazone," Journal of Medicinal Chemistry, vol. 35, No. 20, 1992, pp. 3672-3677 and U.S. Pat. No. 5,869,676. Oral formulations of 3-AP were also described in US20150250776.

Formula I

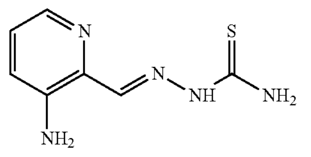

STR00001##

3-AP is a potent inhibitor of ribonucleotide reductase (RR), the rate determining enzyme in the supply of deoxynucleotides (DNA building blocks) for DNA synthesis. DNA synthesis is required for cellular proliferation and DNA repair. Therefore, 3-AP has broad spectrum antitumor activity, and synergizes with antitumor drugs that target DNA. 3-AP is a very strong iron chelator and, in the body, the iron chelate may be the active species that quenches the active site tyrosyl radical required by RR for enzymatic activity. The 3-AP iron chelate is also redox active with several reports in the literature ascribing this property to some of the biological activities of 3-AP.

The mechanism by which 3-AP inhibits RR is thought to be similar to that of hydroxyurea, an agent with clinical antitumor activity against both solid tumors and hematological malignancies. However, 3-AP is 100 to 1000-fold more potent than hydroxyurea in both enzyme and tumor cell-growth inhibition assays and was shown to be active in cell lines selected for resistance to hydroxyurea. The increased activity of 3-AP compared with hydroxyurea is thought to be a consequence of its ability to chelate iron, which is essential to regenerate the tyrosyl-free radical in the M2 subunit that initiates reduction of ribonucleotides.

The synthesis of 3-AP was described in Liu, et al. "Synthesis and Antitumor Activity of Amino Derivatives of Pyridine-2-carboxaldehyde Thiosemicarbazone" ("Liu-1992".) In the final step of synthesis, to a solution of 3-Amino-2-(1.3-dioxolan-2-yl)pyridine (0.80 g, 4.8 mmol) in 10 mL of ethanol, 8 mL of water, and 2 mL of concentrated hydrochloric acid was added 0.48 g (5.3 mmol) of thiosemicarbazide. The mixture was stirred at room temperature overnight, refluxed for 1 hour, cooled, and filtered. The crude yellow hydrochloride salt was dissolved in 50 mL of hot water and filtered. To the hot filtrate was added 10 mL of 5% sodium bicarbonate solution. The mixture was stirred at room temperature for 1 hour, filtered, and washed with water, followed by ethanol: yield 0.72 g (77%), mp 240-241 degrees Celsius, MS m/z 194 (M+). Liu-1992 does not describe or characterize a crystalline 3-AP, and purity and degradation products are also not described. Finally, Liu-1992 does not describe oral compositions of 3-AP.

In U.S. Pat. No. 5,869,676, synthesis of 3-AP by different methods is described including (1) conversion of the 2-carboxaldehyde into an acetal and reduction of the nitro group at position 3 before the coupling of the thiosemicarbazide at the 2-position followed by simple reduction of the nitro group, (2) syntheses of 3-AP from 2-chloro-3-nitropyridine and (3) from 2-chloro-3-aminopyridine. In the final step of synthesis, the crude solid was dissolved in 30 mL of water and filtered. The filtrate was then adjusted to pH 7.5 with saturated $NaHCO_3$ solution and stirred at room temperature for 30 minutes, filtered, washed with water, ethanol and ether. The resulting yellow solid was further extracted with THF several times. The combined THF extracts were evaporated off and the residue was dried in vacuo to provide 81 to 93% 3-AP. In the '676 reference, a crystalline fine particle form of 3-AP is not formed, described or characterized. Purity and degradation products are also not described. Finally, oral compositions are not described.

In Kowol, et al. ("Kowol-2009") "Impact of Metal Coordination on Cytotoxicity of 3-Aminopyridine-2-carboxaldehyde", metal complexes of 3-AP were synthesized and characterized. 3-AP was synthesized from the commercially available 3-amino-2-bromopyridine with the amino group was protected with ditert-butyl dicarbonate in dry THF, using sodium bis-(trimethylsilyl)amide as a base. Treatment of the tert-Boc protected 3-amino-2-bromopyridine with n-BuLi in dry THF resulted in the lithiated species, which was further reacted with N-formylpiperidine to give the carboxaldehyde. Finally, the condensation reaction with thiosemicarbazide in ethanol in the presence of concentrated HCl afforded 3-AP hydrochloride, which was converted into the free base by treatment with sodium bicarbonate. A 3-AP single crystal (0.30×0.15×0.04 mm), as well as iron(III) and gallium(III) complexes were studied by X-ray crystallography to characterize metal complex bond lengths. In the Kowol-2009 reference, crystalline 3-AP fine particle powder is not formed, described or characterized by x-ray diffraction (XRD). Purity and degradation products are also not described. Finally, oral compositions are not described.

In US patent application 20150250776, compositions comprising particles comprising 3-AP and at least one controlled-release polymer, wherein the 3-AP is encapsulated by the at least one controlled-release polymer, and pharmaceutical compositions is described. In the '776 reference, a crystalline fine particle form of 3-AP is not formed, described or characterized, as well as purity of 3-AP or degradation products.

In Plamthottam, et al. ("Plamthottam-2019") "Activity and electrochemical properties: iron complexes of the anticancer drug triapine and its analogs" (JBIC, Journal of Biological Inorganic Chemistry 2019, 24(5), 621-632), synthesis of 12 analogs of 3-AP, inhibition of RNR in vitro, and the electronic properties of their iron complexes is described. Complexation with Iron at different concentrations is studied by UV-Vis and in vitro cell culture experiments. In the Plamthottam-2019 reference, crystalline 3-AP fine particle powder is not formed, described or characterized. Purity and degradation products are also not described. Finally, oral compositions are not described.

In Taylor, et al. ("Taylor-2024") "Dose finding, bioavailability, and PK-PD of oral triapine with concurrent chemoradiation for locally advanced cervical cancer and vaginal cancer (ETCTN 9892)" (Cancer Chemotherapy and Pharmacology (2024) Dec. 14; 95(1):4), crystalline fine particle 3-AP formulations demonstrated an oral bioavailability of 59%.

Oral administration of drugs, such as 3-AP, is generally preferred over intravenous administration for reasons of patient comfort and compliance. However, many drugs, including 3-AP, have poor solubility in aqueous solutions, and are thus variably absorbed when delivered orally. Consequently, many such drugs, including 3-AP, are administered through more invasive routes, such as intravenous routes. There has been substantial effort in the last decade to produce crystalline drug particles from 100 nanometers to a few hundred microns because of their improved and controlled dissolution properties and ability to be absorbed more efficiently. Through a number of experiments, the present inventors have surprisingly discovered new solid forms of 3-AP forms, comprising the fine particle crystalline form of the 3-AP, with improved stability and reduced rates of degradation from oxidation. This crystalline fine particle form is unexpectedly more suitable for formulation processing, storage, industrial production, and has reproducible bioavailability. Compared with the known solid form of 3-AP described in U.S. Pat. No. 5,869,676, the fine particle crystalline form of the 3-AP in present invention has at least one or more superior properties and achieve unexpected effects relevant for oral administration. Specific improvements are, for example, better dispersibility in water, higher dissolution rate, higher purity, improved room temperature shelf-life stability, lower hygroscopicity, better flowability and/or favorable processing and handling characteristics. In some embodiments, the new crystalline fine particle form in the present invention has improved stability.

SUMMARY OF THE INVENTION

The present disclosure addresses this need by providing crystalline 3-AP preparations relating to compositions comprising the compound of Formula I, methods for preparation and the treatment for cancer. In certain aspects, the present disclosure provides novel methods of preparing the compound of Formula I, or 3-aminopyridine-2-carboxaldehyde thiosemicarbazone (3-AP, Triapine), crystalline fine particle forms of 3-AP, and compositions comprising them. In certain aspects, the present disclosure provides novel crystalline fine particle forms of 3-AP which may provide advantages including improved bioavailability and stability relative to other crystalline or amorphous forms. In other aspects, the present disclosure provides oral dosage forms comprising the crystalline fine particle form of 3-AP and excipients with improved stability. In additional aspects, the present disclosure provides novel methods of synthesizing a novel crystalline fine particle form of 3-AP, preparing crystalline 3-AP particle delivery systems (PDS), and preparing novel final dosage forms (FDF) of crystalline fine particle forms of 3-AP. In certain aspects, the present disclosure provides novel crystalline fine particle forms of 3-AP which may provide advantages including improved bioavailability and stability relative to other crystalline or amorphous forms.

In certain aspects, the present disclosure provides a composition comprising a crystalline form of the compound of Formula I:

Formula I

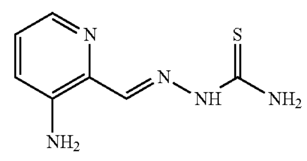

STR00001##

In some embodiments, a composition comprising a crystalline form of a compound of Formula I: ##STR00001 ##, wherein the crystalline form is Form I characterized by an x-ray powder diffraction pattern comprising major peaks at 10.4+/−0.3 degrees, 18.1+/−0.3 degrees and 30.9+/−0.3 degrees two theta, and optionally further comprising at least one peak selected from 25.0+/−0.3 degrees, 25.5+/−0.3 degrees and 27.1+/−0.3 degrees two theta. In some embodiments, the x-ray powder diffraction pattern further comprises at least one peak selected from 19.7+/−0.3 degrees, 32.4+/−0.3 degrees and 50.0 degrees two theta. The x-ray powder diffraction pattern may further comprise peaks at 10.4+/−0.3 degrees, 18.1+/−0.3 degrees, 30.9+/−0.3 degrees 25.0+/−0.3 degrees, 25.5+/−0.3 degrees and 27.1+/−0.3 degrees two theta.

In some embodiments, the crystalline form of the compound of Formula I is Form I characterized by an x-ray powder diffraction pattern substantially as set forth in FIG. 4A, FIG. 4B, FIG. 5A, or FIG. 5B. In some embodiments, greater than 90% by weight of the compound of Formula I in the composition may be crystalline and the crystalline form is Form I. In some embodiments, the compound of Formula I is Form I and is present in an amount ranging from about 0.01% to about 99.99% by mass of the composition. In some embodiments, particles of the crystalline form of the compound of Formula I in the composition have an average diameter of less than about 1 mm, 0.5 mm, or 0.3 mm. In some embodiments, the composition is sieved to obtain particles of the crystalline form of the compound of Formula I having an average diameter of less than about 1 mm, 0.5 mm, or 0.3 mm.

In some embodiments, the composition comprising the compound of Formula I is stable for at least 12 months at about 5 degrees Celsius (refrigeration) or at about 25 degrees Celsius (room temperature). In some embodiments, stability of the composition is determined by the formation of degradation products of the compound of Formula I in the composition. In further embodiments, the formation of degradation products of the compound of Formula I in the composition is less than 0.5 weight % (each degradation product) per year at about 5 degrees Celsius (refrigeration)

or at about 25 degrees Celsius (room temperature). In further embodiments, the formation of degradation products of the compound of Formula I in the composition is less than 0.5 weight % (total of degradation products) per year at about 5 degrees Celsius (refrigeration) or at about 25 degrees Celsius (room temperature). In additional embodiments, the compound degradation product(s) in the composition are a compound of Formula II: 3-amino-2-{(E)-[(2E)-(aminomethylidene)hydrazinylidene]methyl}-1-hydroxypyridin-1-ium and/or a compound of Formula III: 3-amino-2-[(E)-(2-carbamothioylhydrazinylidene)methyl]-1-hydroxypyridin-1-ium. In some embodiments, the composition comprises a compound impurity of Formula IV: Fe(II) complex with two 3-AP molecules. In some embodiments, the composition comprises less than 0.5% by weight of the compound of Formula II, if present, and less than 0.5% by weight of the compound of Formula III, if present. In some embodiments, the composition comprises less than 0.5% by weight of the compound impurity of Formula IV, if present.

Formula II

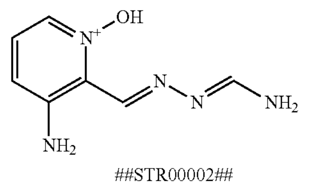

STR00002##

Formula III

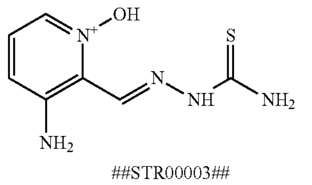

STR00003##

Formula IV

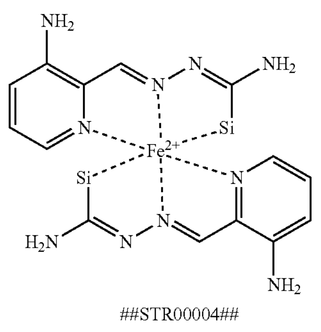

STR00004##

In some embodiments, a composition is described comprising a compound of Formula I, wherein the compound of Formula I comprises a crystalline form of the compound of Formula I and wherein the composition further comprises a compound of Formula II, a compound of Formula III, and/or a compound of Formula IV, wherein the composition comprises less than 0.5 weight % of the compound of Formula II, if present, less than 0.5 weight % of the compound of Formula III, if present, and less than 0.5 weight % of the compound of Formula IV, if present.

In certain embodiments, a particulate delivery system (PDS) is described comprising a crystalline form of a compound of Formula I and at least one pharmaceutically acceptable excipient. In certain embodiments, the particulate delivery system (PDS) comprises a crystalline form of a compound of Formula I, wherein the crystalline form of the compound of Formula I is Form I characterized by an x-ray powder diffraction pattern comprising at least one peak selected from 10.4+/−0.3 degrees, 18.1+/−0.3 degrees and 30.9+/−0.3 degrees two theta. In certain embodiments, the x-ray powder diffraction pattern further comprises at least one peak selected from 25.0+/−0.3 degrees, 25.5+/−0.3 degrees and 27.1+/−0.3 degrees two theta. In certain embodiments, the x-ray powder diffraction pattern further comprises at least one peak selected from 19.7+/−0.3 degrees, 32.4+/−0.3 degrees and 50.0 degrees two theta. In certain embodiments, the x-ray powder diffraction pattern further comprises peaks at 10.4+/−0.3 degrees, 18.1+/−0.3 degrees, 30.9+/−0.3 degrees 25.0+/−0.3 degrees, 25.5+/−0.3 degrees and 27.1+/−0.3 degrees two theta. In certain embodiments, the crystalline form of a compound of Formula I is characterized by an x-ray powder diffraction pattern substantially as set forth in FIG. 4A or FIG. 4B.

In certain embodiments, the particulate delivery system comprises a compound of Formula I wherein greater than 90% by weight of the compound of Formula I is the crystalline form of Form I. In certain embodiments, the particulate delivery system comprises the compound of Formula I, wherein the compound of Formula I is the crystalline form of Form I and is present in the particulate delivery system in an amount ranging from about 0.01% to about 99.99% by mass, about 10% to about 90% by mass, or about 10% to about 50% by mass.

In certain embodiments, the particulate delivery system is formulated for oral, parenteral, or topical delivery. In certain embodiments, the particulate delivery system is formulated for oral delivery as a tablet, a caplet, a capsule, or a pill.

In certain embodiments, the particulate delivery system comprises a compound of Formula I and optionally at least one pharmaceutically acceptable excipient, wherein the compound of Formula I comprises a crystalline form of the compound of Formula I, wherein particles of the crystalline form of the compound of Formula I have an average diameter of less than about 1 mm, 0.5 mm, or 0.3 mm. In certain embodiments, the particulate delivery system comprises a mixture of a compound of Formula I and at least one pharmaceutically acceptable excipient, wherein the compound of Formula I comprises a crystalline form of the compound of Formula I and wherein particles of the mixture have an average diameter of less than about 1 mm, 0.5 mm, or 0.3 mm. In certain embodiments, the pharmaceutically acceptable excipient is a polymer, a water-soluble polymer, and is chosen from magnesium stearate, starch, or polyethylene glycol. In certain embodiments, the particulate delivery system includes a second excipient and is chosen from magnesium stearate, starch, or polyethylene glycol.

In certain embodiments, the particulate delivery system is formulated for oral administration and may comprise 0.01 mg to about 200 mg of the compound of Formula I. In certain embodiments, the particulate delivery system contains the compound of Formula I and the particulate delivery system is stable for at least 12 months at about 5 degrees Celsius (refrigeration) or at about 25 degrees Celsius (room temperature). In some embodiments, stability of the particulate delivery system is determined by the formation of degradation products of the compound of Formula I in the particulate delivery system. In further embodiments, the formation of degradation product(s) in the particulate delivery system is less than 0.5 weight % per year (each degradation product) at about 5 degrees Celsius (refrigeration) or at about 25 degrees Celsius (room temperature). In further embodiments, the formation of degradation product(s) in the particulate delivery system is less than 0.5 weight % per year (total of degradation products) at about 5 degrees Celsius (refrigeration) or at about 25 degrees Celsius (room temperature). In further embodiments, the compound degradation product(s) in the particulate delivery system are a compound of Formula II: 3-amino-2-{(E)-[(2E)-(aminomethylidene)hydrazinylidene]methyl}-1-hydroxypyridin-1-ium and/or a compound of Formula III: 3-amino-2-[(E)-(2-carbamothioylhydrazinylidene)methyl]-1-hydroxypyridin-1-ium. In some embodiments, the particulate delivery system comprises a compound impurity of Formula IV: Fe(II) complex with two 3-AP molecules. In further embodiments, the particulate delivery system comprises less than 0.5 weight % of the compound of Formula II, if present, and less than 0.5 weight % of the compound of Formula III, if present. In some embodiments, the particulate delivery system comprises less than 0.5 weight % of the compound of Formula IV, if present.

In some embodiments, a particulate delivery system is described comprising a compound of Formula I, wherein the compound of Formula I comprises a crystalline form of the compound of Formula I and wherein the particulate delivery system further comprises a compound of Formula II, a compound of Formula III, and/or a compound of Formula IV, wherein the particulate delivery system comprises less than 0.5 weight % of the compound of Formula II, if present, less than 0.5 weight % of the compound of Formula III, if present, and less than 0.5 weight % of the compound of Formula IV, if present.

The present invention also describes methods method of making the particulate delivery system comprising the compound of Formula I and compositions thereof, comprising: blending the compound of Formula I together with an excipient to form a mixture; processing said mixture to form coarse particles having an average diameter ranging from about 0.1 mm to about 5 mm; and grinding or milling said coarse particles to form particles having an average diameter less than about 0.5 mm. In a further embodiment, present invention also describes a method of making the particulate delivery system comprising the compound of Formula I and composition thereof, comprising: blending the compound of Formula I together with a polymer to form a mixture; processing said mixture to form coarse particles having an average diameter ranging from about 0.1 mm to about 5 mm; and milling said coarse particles to form particles having an average diameter less than about 1 micrometers.

In certain aspects, the present disclosure provides a method of treating cancer, comprising administering an effective amount of the compound of Formula I or a composition thereof to a patient in need thereof. In a further embodiment, the present disclosure provides a method of treating cancer in combination with another chemotherapeutic agent or radiation, comprising administering an effective amount of the compound of Formula I or a composition thereof to a patient in need thereof.

In certain embodiments, the present disclosure provides a method of treating cancer in a subject, the method comprising administering to the subject a composition comprising a crystalline form of a compound of Formula I, wherein at least 90% by weight of the compound of Formula I is the crystalline form of Form I characterized by an x-ray powder diffraction pattern comprising major peaks at 10.4+/−0.3 degrees, 18.1+/−0.3 degrees and 30.9+/−0.3 degrees two theta, and wherein the composition is prepared by blending the compound of Formula I together with an excipient to form a mixture; processing said mixture to form coarse particles having an average diameter ranging from about 0.1 mm to about 5 mm; and grinding or milling said coarse particles to form particles having an average diameter less than about 500 micrometers.

In another aspect, the present disclosure provides a method of making a composition comprising crystalline fine particle Form I of 3-AP, the method comprising blending the crystalline fine particle Form I of 3-AP together with a polymer to form a mixture.

In one aspect, the present disclosure provides an industrially scalable process for manufacturing crystalline fine particle Form I of a compound of Formula I, comprising the steps of:

(a) Boc protection of 3-(tert-Butoxycarbonylamino)-2-bromopyridine with a 1M solution of Sodium bis (trimethylsilyl) amide (NaHNDS) in THF (2.1 equiv.) added dropwise to a solution of 3-amino-2-bromopyridine compound 1 (1 equiv.) and di-t-butylcarbonate in THF at 0 degrees Celsius, (b) synthesis of aldehyde 3-(N-tert-Butoxycarbonylamino)-2-pyridinecarboxaldehyde by treatment of the tert-Boc protected 3-amino-2-bromopyridine with n-BuLi in anhydrous THF resulting in the lithiated species, which was further reacted with N-formylpiperidine at low temperature (−65 to −70 degrees Celsius), and (c) synthesis of 3-AP by condensation of aldehyde 5 with thiosemicarbazide (6) in ethanol and water in the presence of concentrated HCl and deprotection to prepare 3-AP hydrochloride, which is converted into the free base by basification with sodium bicarbonate solution, cooled to room temperature overnight followed by 1-5 degrees Celsius for 1 hour for crystallization, washed with cold water, ethanol, and diethyl ether, and then vacuum dried to obtain coarse particles, and whereas the crystalline form of a compound of Formula I is Form I, and wherein the crystalline form of Form I is obtained by grinding the course particles or sieving.

In some embodiments, the present disclosure provides conversion to 3-AP by basification of 3-AP hydrochloride with sodium bicarbonate solution, cooled to room temperature overnight followed by 1-5 degrees Celsius for 1 hour for crystallization, washed with cold water, ethanol, and diethyl ether, and then vacuum dried followed by separation and drying, wherein greater than 90% of the compound of Formula I obtained from the process is the crystalline form of Form I. In a further embodiment, the present disclosure provides conversion to 3-AP by dissolving 3-AP hydrochloride in sodium bicarbonate solution at a first temperature from about 20 degrees Celsius to about 100 degrees Celsius and then cooling the solution to a second temperature. In a further embodiment, the present disclosure provides further crystallization by cooling the solution to a temperature ranging from about 0 degrees Celsius to about 10 degrees Celsius. In a further embodiment, the present disclosure provides crystallization by cooling the solution to a temperature ranging from about 0 degrees Celsius to about 20 degrees Celsius for 0.5 hours to 10 days. In a further embodiment, the present disclosure provides crystallization by cooling the solution to a temperature ranging from about 0 degrees Celsius to about 20 degrees Celsius for 1 to 4 hours. In a further embodiment, the present disclosure provides separation of the crystalline solid may be by filtration, decanting, aspiration, or any suitable method. In yet another further embodiment, the present disclosure provides separation of the crystalline solid may be by filtration washed with solvent, and dried in vacuo to constant weight. In a further embodiment, the present disclosure provides the crystalline solid washed one or more times with cold water, ethanol, and diethyl ether. In a further embodiment, the present disclosure provides the crystalline solid dried under reduced pressure, including at a temperature ranging from about 20 degrees Celsius to about 100 degrees Celsius.

In another embodiment, the present disclosure provides a crystal form of a compound of Formula I:

Formula I

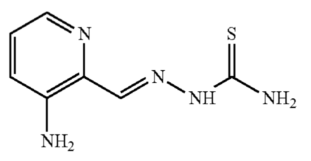

STR00001##

- wherein the crystal form of the compound of Formula I is Form I characterized by an x-ray powder diffraction pattern further comprising at least one peak selected from 10.4+/−0.3 degrees, 18.1+/−0.3 degrees, 25.0+/−0.3 degrees, 25.5+/−0.3 degrees, 27.1+/−0.3 degrees and 30.9+/−0.3 degrees two theta, and
- wherein greater than 90% by weight of the compound of Formula I is Form I.

In another embodiment, the present disclosure provides a crystalline form of a compound of Formula I:

Formula I

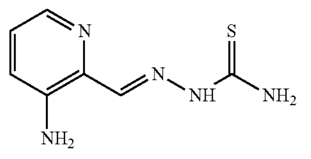

STR00001##

- wherein the crystalline form of the compound of Formula I is Form I characterized by an x-ray powder diffraction pattern comprising at least one peak selected from 10.4+/−0.3 degrees, 18.1+/−0.3 degrees, 25.0+/−0.3 degrees, 25.5+/−0.3 degrees, 27.1+/−0.3 degrees and 30.9+/−0.3 degrees two theta,
- wherein greater than 90% by weight of the compound of Formula I is Form I,
- wherein the particles of the crystalline form of the compound of Formula I have an average diameter of less than about 500 μm, and
- wherein the compound is stable for at least 12 months at about 5 degrees Celsius (refrigeration) or at about 25 degrees Celsius (room temperature).

In another embodiment, the present disclosure provides methods of making the particulate delivery system comprising a compound of Formula I, comprising: blending the the compound of Formula I together with an excipient to form a mixture; processing said mixture to form coarse particles having an average diameter ranging from about 0.1 mm to about 5 mm; and grinding or milling said coarse particles to form particles having an average diameter less than about 0.5 mm. In a further embodiment, present invention also describes a method of making the particulate delivery system comprising the compound of Formula I, comprising: blending the compound of Formula I together with a polymer to form a mixture; processing said mixture to form coarse particles having an average diameter ranging from about 0.1 mm to about 5 mm; and milling said coarse particles to form particles having an average diameter less than about 1 micrometers.

In yet another embodiment, the present disclosure provides a particulate delivery system comprising a mixture of a compound of Formula I and at least one pharmaceutically acceptable excipient,

- wherein the compound of Formula I comprises a crystalline form of the compound of Formula I,
- wherein greater than 90% by weight of the compound of Formula I is Form I characterized by an x-ray powder diffraction pattern comprising major peaks at 10.4+/−0.3 degrees, 18.1+/−0.3 degrees, 25.0+/−0.3 degrees, 25.5+/−0.3 degrees, 27.1+/−0.3 degrees and 30.9+/−0.3 degrees two theta,
- wherein the mixture has an average diameter of less than about 500 μm,
- wherein the compound of Formula I is stable for at least 12 months at about 5 degrees Celsius (refrigeration) or at about 25 degrees Celsius (room temperature), and
- wherein the particulate delivery system is formulated for oral delivery.

In yet another embodiment, the present disclosure provides a particulate delivery system comprising a compound of Formula I and at least one pharmaceutically acceptable excipient,

- wherein the compound of Formula I comprises a crystalline form of the compound of Formula I,
- wherein greater than 90% by weight of the compound of Formula I is Form I characterized by an x-ray powder diffraction pattern comprising major peaks at 10.4+/−0.3 degrees, 18.1+/−0.3 degrees, 25.0+/−0.3 degrees, 25.5+/−0.3 degrees, 27.1+/−0.3 degrees and 30.9+/−0.3 degrees two theta,
- wherein the compound of Formula I has an average diameter of less than about 500 μm,
- wherein the compound of Formula I is stable for at least 12 months at about 5 degrees Celsius (refrigeration) or at about 25 degrees Celsius (room temperature), and
- wherein the particulate delivery system is formulated for oral delivery.

In yet another embodiment, the present disclosure provides an industrially scalable process for manufacturing a compound of Formula I wherein the compound of Formula I comprises a crystalline form of the compound of Formula I, comprising the steps of:

(a) Boc protection of 3-(tert-Butoxycarbonylamino)-2-bromopyridine with a 1M solution of Sodium bis (trimethylsilyl) amide (NaHNDS) in THF (2.1 equiv.) added dropwise to a solution of 3-amino-2-bromopyridine compound 1 (1 equiv.) and di-t-butylcarbonate in THF at 0 degrees Celsius, (b) synthesis of aldehyde 3-(N-tert-Butoxycarbonylamino)-2-pyridinecarboxaldehyde by treatment of the tert-Boc protected 3-amino-2-bromopyridine with n-BuLi in anhydrous THF resulting in the lithiated species, which was further reacted with N-formylpiperidine at low temperature (−65 to −70 degrees Celsius), and (c) synthesis of 3-AP by condensation of aldehyde with thiosemicarbazide in ethanol and water in the presence of concentrated HCl and deprotection afforded 3-AP hydrochloride, which is converted into the free base by basification with sodium bicarbonate solution, cooled to room temperature overnight followed by 1-5 degrees Celsius for 1 hour for crystallization, washed with cold water, ethanol, and diethyl ether, and then vacuum dried to obtain coarse particles, wherein crystallization is performed by cooling the solution to 10 degrees Celsius to about 30 degrees Celsius for 18 to 24 hours, followed by a temperature ranging from about 0 degrees Celsius to about 10 degrees Celsius for 1 to 4 hours, wherein the crystalline solid is dried under reduced pressure at a temperature ranging from about 20 degrees Celsius to about 100 degrees Celsius, wherein the crystalline form of the compound of Formula I is obtained by grinding the coarse particles or sieving, and wherein greater than 90% by weight of the compound of Formula I is Form I.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

I. Terminology

Figure 1A:
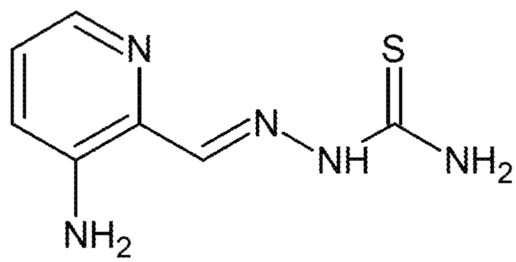
FIG. 1A is chemical structure of 3-AP, also known as Triapine, a compound of Formula I: ##STR00001 ##, also referred to as 3-aminopyridine-2-carboxaldehyde thiosemicarbazone and (2E)-2-[(3-aminopyridin-2-yl)methylidene] hydrazine-1-carbothioamide.
Figure 1B:
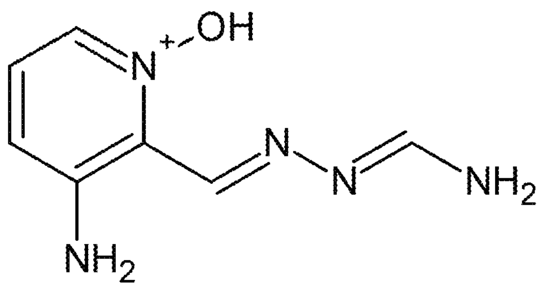
FIG. 1B is a 3-AP degradation product having the structure of Formula II: ##STR00002 ##: 3-amino-2-{(E)-[(2E)-(aminomethylidene)hydrazinylidene] methyl}-1-hydroxypyridin-1-ium.
Figure 1C:
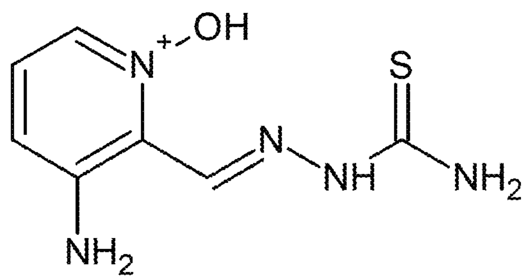
FIG. 1C is a 3-AP degradation product having the structure of Formula III: ##STR00003 ##: 3-amino-2-[(E)-(2-carbamothioylhydrazinylidene)methyl]-1-hydroxypyridin-1-ium.
Figure 1D:
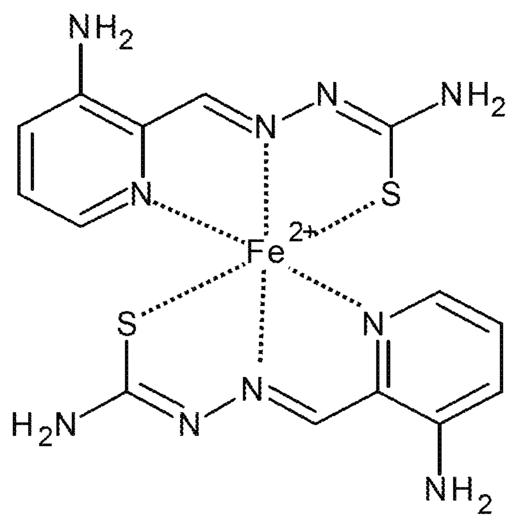
FIG. 1D is a 3-AP impurity having the structure of Formula IV: ##STR00004 ##: Fe(II) complex with two 3-AP molecules.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical, and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of iron include $^{54}Fe$, $^{56}Fe$, $^{57}Fe$ and $^{58}Fe$.

A significant change is any detectable change that is statistically significant in a standard parametric test of statistical significance such as Student's T-test, where $p<0.05$.

II. Synthesis of Crystalline Fine Particle Form I of 3-AP

The disclosure includes the following embodiments, which should not be construed as limiting. Rather, these embodiments are exemplary and are provided to describe the invention to those skilled in the art. Like reference numerals refer to like elements throughout.

It has been unexpectedly discovered that synthesis of crystalline 3-AP with high purity is obtained using the disclosed three step process, eliminating chromatography purification reported in the literature and U.S. Pat. No. 5,869,676. Efficient synthesis of crystalline 3-AP has been discovered by condensation of aldehyde 3-(N-tert-Butoxycarbonylamino)-2-pyridinecarboxaldehyde with thiosemicarbazide in ethanol and water in the presence of concentrated HCl and deprotection of 3-AP hydrochloride, which is converted into the free base by basification with sodium bicarbonate solution, cooled to room temperature overnight followed by 1-5 degrees Celsius for 1 hour for crystallization, washed with cold water, ethanol, and diethyl ether, and then vacuum dried.

In one aspect, the present disclosure provides an industrially scalable process for manufacturing crystalline 3-AP thereof, comprising the steps of:

(a) Boc protection of 3-(tert-Butoxycarbonylamino)-2-bromopyridine with a 1M solution of Sodium bis (trimethylsilyl) amide (NaHNDS) in THF (2.1 equiv.) added dropwise to a solution of 3-amino-2-bromopyridine compound 1 (1 equiv.) and di-t-butylcarbonate in THF at 0 degrees Celsius, (b) synthesis of aldehyde 3-(N-tert-Butoxycarbonylamino)-2-pyridinecarboxaldehyde by treatment of the tert-Boc protected 3-amino-2-bromopyridine with n-BuLi in anhydrous THF resulting in the lithiated species, which was further reacted with N-formylpiperidine at low temperature (−65 to −70 degrees Celsius), and (c) synthesis of 3-AP by condensation of aldehyde with thiosemicarbazide in ethanol and water in the presence of concentrated HCl and deprotection afforded 3-AP hydrochloride, which is converted into the free base by basification with sodium bicarbonate solution, cooled to room temperature overnight followed by 1-5 degrees Celsius for 1 hour for crystallization, washed with cold water, ethanol, and diethyl ether, and then vacuum dried to obtain coarse particles, and wherein the crystalline fine particle Form I of 3-AP is obtained by grinding the coarse particles or sieving.

The present disclosure provides conversion to 3-AP by basification of 3-AP hydrochloride with sodium bicarbonate solution, cooled to room temperature overnight followed by 1-5 degrees Celsius for 1 hour for crystallization, washed with cold water, ethanol, and diethyl ether, and then vacuum dried and a mother liquor followed by separation and drying, wherein greater than 90% by weight of the compound of Formula I is the crystalline form of Form I. In a further embodiment, the present disclosure provides conversion to 3-AP by dissolving 3-AP hydrochloride in sodium bicarbonate solution at a first temperature from about 20 degrees Celsius to about 100 degrees Celsius and then cooling the solution to a second temperature. In a further embodiment, the present disclosure provides further crystallization by cooling the solution to a temperature ranging from about 0 degrees Celsius to about 10 degrees Celsius. In a further embodiment, the present disclosure provides crystallization by cooling the solution to a temperature ranging from about 0 degrees Celsius to about 20 degrees Celsius for 0.5 hours to 10 days. In a further embodiment, the present disclosure provides crystallization by cooling the solution to a temperature ranging from about 0 degrees Celsius to about 20 degrees Celsius for 1 to 4 hours. In a further embodiment, the present disclosure provides separation of the crystalline solid may be by filtration, decanting, aspiration, or any suitable method. In yet another further embodiment, the present disclosure provides separation of the crystalline solid may be by filtration washed with solvent, and dried in vacuo to constant weight. In a further embodiment, the present disclosure provides the crystalline solid washed one or more times with cold water, ethanol, and diethyl ether. In a further embodiment, the present disclosure provides the crystalline solid dried under reduced pressure, including at a temperature ranging from about 20 degrees Celsius to about 100 degrees Celsius.

III. Crystalline Forms

In certain aspects, the present disclosure provides crystalline fine particle Form I of 3-AP. The present disclosure further provides pharmaceutical compositions of 3-AP comprising the crystalline forms described herein. A crystalline form of 3-AP may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of 3-AP may provide advantages such as: improving the manufacturing process of an active agent or the stability or storability of a drug product form of the compound or an active ingredient, and/or having suitable bioavailability and/or stability as an active agent.

The use of certain solvents and fractional crystallization methods has been found to produce different polymorphic forms of 3-AP, including polymorphic Form I, which may exhibit one or more favorable characteristics described above. The processes for the preparation of the polymorphs described herein, and characterization of these polymorphs are described in greater detail below.

Figure 4:
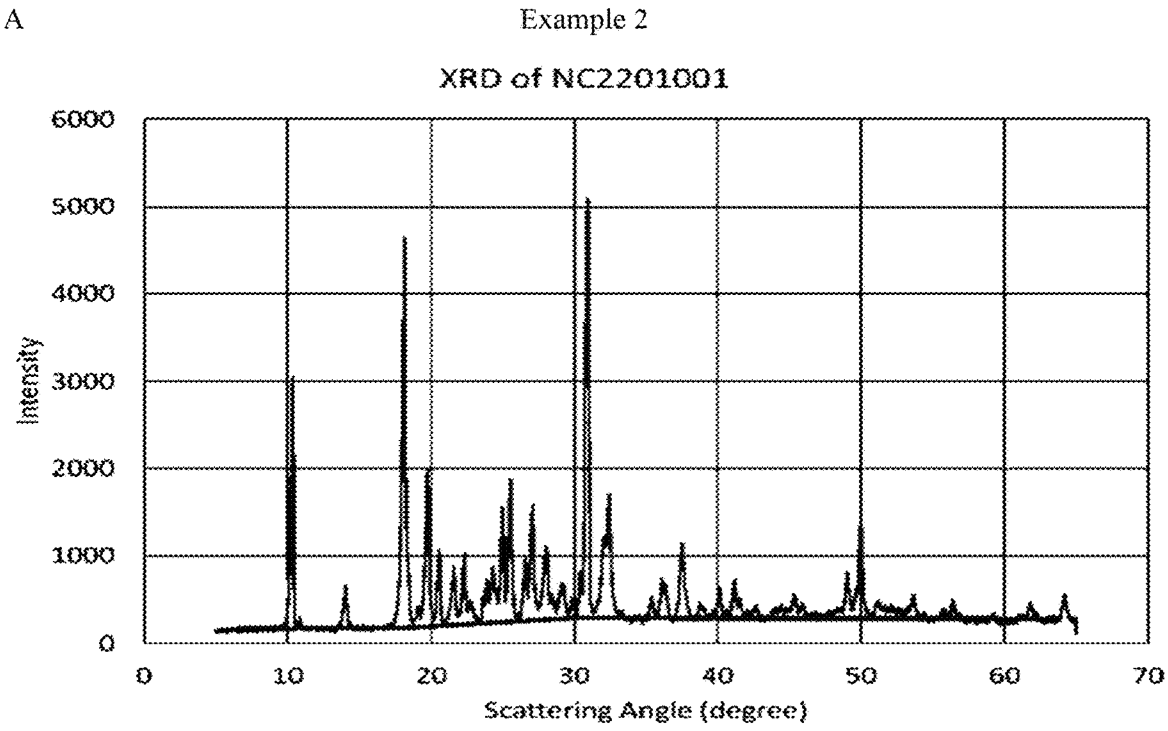
FIG. 4 is the XRD pattern of Example 2 (A) crystalline fine particle Form I of 3-AP Lot NC2201001 and (B) crystalline fine particle Form I of 3-AP scale-up batch Lot NC2205002.
Figure 4:
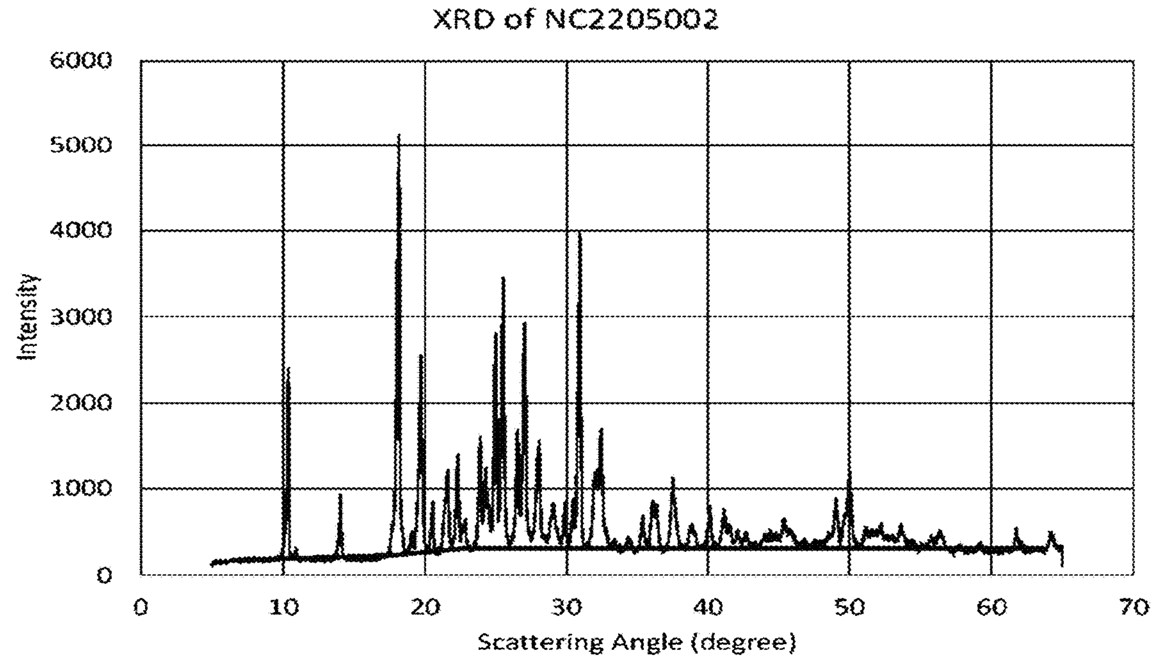

In certain aspects, the present disclosure provides 3-AP wherein at least 90% by weight of 3-AP is polymorphic Form I of 3-AP. In some embodiments, polymorphic Form I exhibits an x-ray diffraction (XRD) pattern substantially as shown in FIG. 4A or 4B. In some embodiments, polymorphic Form I has an XRD pattern comprising at least two, at least three, at least four, at least five, or at least six of the major peaks as the XRD pattern substantially as shown in FIG. 4A or 4B. The crystalline structure of the present invention is substantially pure, unitary, and substantially free of any other crystal form or amorphous state. "Substantially pure" in the present invention when used in reference to a new crystal form means that at least 80% (by weight) of the present compound, more preferably at least 90% (by weight), and especially at least 95% (by weight), especially at least 99% (by weight) is the new crystal form.

The term "substantially as shown in" when referring, for example, to an XRD pattern, includes a pattern that is not necessarily identical to those depicted herein, but that falls within the limits of experimental error or deviations when considered by one of ordinary skill in the art. The relative intensities of XRD peaks can vary, depending upon the particle size, the sample preparation technique, the sample mounting procedure and the particular instrument employed. The crystalline form in the present invention means that the compound is confirmed by the X-ray powder diffraction pattern characterization shown and has a unique and ordered molecular arrangement or configuration within the crystal lattice. It is well known to those skilled in the art that the experimental error depends on the instrument conditions, sample preparation and sample purity. The 2 theta angle of the peaks in the XRD pattern usually varies slightly depending on the instrument and sample. The difference in peak angle may differ by 1 degree, 0.8 degrees, 0.5 degrees, 0.3 degrees, 0.1 degrees, etc. according to different instruments, different samples, etc. Generally, the tolerance is +/−0.2 degrees. Therefore, the difference in peak angle cannot be used as the sole criterion. The relative intensity of peaks may vary with samples, sample preparation, and other experimental conditions, so the order of peak intensities cannot be the sole or decisive factor. The influence of experimental factors such as sample height will cause the overall shift of the peak angle, which usually allows a certain shift. Therefore, those skilled in the art can understand that any crystal form having the same or similar characteristic peaks as the X-ray powder diffraction pattern of the present invention belongs to the scope of the present invention. "Single crystalline form" refers to a single crystal form as determined by X-ray powder diffraction.

Moreover, instrument variation and other factors can affect the two theta values. Accordingly, when a specified two theta angle is provided, it is to be understood that the specified two theta angle can vary by the specified value+/−0.5 degrees, such as +/−0.4 degrees, +0.3 degrees, +/−0.2 degrees, or +/−0.1 degrees theta. As used herein, "major peak" refers to an XRD peak with a peak intensity greater than baseline, such as greater than 100 or 500 depending on the baseline noise and other test factors listed above.

In certain aspects, the present disclosure provides at least 90% by weight of 3-AP compound of Formula I in the composition that is a crystalline form. Crystalline Form I may be characterized by an x-ray powder diffraction pattern comprising major peaks at 10.4+/−0.3 degrees, 18.1+/−0.3 degrees and 30.9+/−0.3 degrees two theta, and optionally further comprising at least one peak selected from 25.0+/−0.3 degrees, 25.5+/−0.3 degrees and 27.1+/−0.3 degrees two theta. In some embodiments, the x-ray powder diffraction pattern further comprises at least one peak selected from 19.7+/−0.3 degrees, 32.4+/−0.3 degrees and 50.0 degrees two theta. The x-ray powder diffraction pattern may further comprise peaks at 10.4+/−0.3 degrees, 18.1+/−0.3 degrees, 30.9+/−0.3 degrees 25.0+/−0.3 degrees, 25.5+/−0.3 degrees and 27.1+/−0.3 degrees two theta. In some embodiments, crystalline Form I is characterized by an x-ray powder diffraction pattern substantially as set forth in FIG. 4A or 4B. Greater than 90%, 95% or 99% by weight of the compound of Formula I in the composition may be crystalline Form I. In some embodiments, the composition comprises 0.01 mg to 200 mg of crystalline Form I, such as about 10 mg, 25 mg, 50 mg, 75 mg, 100 mg or 200 mg of crystalline Form I.

In some embodiments, a composition comprising crystalline form of 3-AP comprises 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% 3-AP (wt/wt) or (w/v) of the composition. In some embodiments, a composition comprising crystalline form of 3-AP comprises 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% 3-AP (wt/wt) or (w/v) of the composition.

The compounds and compositions of the present disclosure can be administered to a subject in need thereof by any route known in the art, including without limitation, oral, parenteral, topical, and intraductal delivery. Accordingly, compositions disclosed herein are formulated to be compatible with the intended route of administration.

In some embodiments, the compositions comprising crystalline form of 3-AP further comprise an excipient. Such an excipient can be compatible with the intended route of administration.

IV. Methods of Making a Particle Delivery System (PDS)

The present disclosure also provides a method of making a composition of the present disclosure comprising particles of the crystalline form of 3-AP encapsulated by an excipient, the method comprising:

(a) blending crystalline form of 3-AP together with an excipient to form a mixture;
(b) processing said mixture to form coarse particles having an average diameter ranging from about 0.1 mm to about 5 mm; and
(c) grinding or milling said coarse particles to form particles having an average diameter less than about 500 micrometers.

In certain embodiments, the particles have an average diameter ranging from about 0.1 microns to about 0.1 mm. Particulate materials, also designated as "particles", to be produced in accordance with this disclosure are those in which small nanometer to micrometer size particles may be desirable. Examples may include nanoparticles and microparticle forms of pharmaceuticals, including crystalline form of 3-AP. The possibilities and combinations are numerous.

In one embodiment, a system for preparing a composition of the present disclosure may include grinding the crystalline form of 3-AP in a mortar and pestle or with a ball mill. In another embodiment a system for preparing a composition of the present disclosure may include a venturi-type nozzle or 'Tee' valve to introduce cryogenic gas to, for example, a jet mill. Without wishing to be bound by any particular theory, combinations of dry gases at cryogenic temperatures (generally below 0 degrees C.) before introduction into the jet mill may be used to eliminate moisture-induced agglomeration, as well as promote brittle fracture of particles upon impaction, and has been observed to act synergistically to produce a marked improvement in the particle size reduction efficiency. Cryogenic liquids suitable for use in this method include liquid argon, liquid nitrogen, liquid helium or any other liquified gas having a temperature sufficiently low to produce brittle fracture of particles. The cryogenic liquid may also prevent milling losses and thermal damage to the feed material that would otherwise be caused by the volatization or overheating of constituent ingredients.

In one embodiment, a powder is placed in a temperature-controlled vessel, such as a jacketed hopper or a screw-feeder or is frozen beforehand. The cryogenic liquid and gas inputs are opened, and the flow and temperature are set to the desired process conditions. The cryogenic gas input system, for example liquid nitrogen mixed with nitrogen gas, may be connected to a standard commercial jet mill, such as a Trost Gem-T, Trost T-15, Fluid Air Aljet, Hosikawa Alpine AS Spiral Jet Mill, Sturtevant Micronizer, or similar system, as the main carrier gas in a variety of gas input setups. Pre-run setup of the system may include attaching a temperature probe or flowmeter, such as a TSI Model 4040 Flowmeter or similar system, at the gas input or to the top of the cyclone (in place of air relief bag), setting the carrier gas on different input pressures and documenting the gas flow and temperature measurements (CFM). The milling process may be started by turning on the powder feeder and after passing powder through the milling region, the jet-milled powder is collected in the cup or similar receiver unit (typically particles ~1-10 microns) or from the bag above the cyclone (particles<1 micron), depending on the exact run conditions. Particles with diameters ranging from less than about 1 micron to about 10 microns may be produced by running the powder from the cup through the jet-mill under similar run conditions multiple times, or passes, to obtain the desired particle size.

In certain embodiments, the particles may have an average diameter ranging from about 0.1 mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns and may be able to pass through a 50-mesh sieve. In certain embodiments, the particles have a diameter of about 0.6 mm or less.

In certain embodiments, the controlled-release polymer is heated prior to blending with the crystalline form of 3-AP.

In some embodiments, the present disclosure provides a method of making a composition of the present disclosure comprising particles of the crystalline form of 3-AP encapsulated by a controlled-release polymer using a process wherein the process is at least partially a continuous manufacturing process. The method may comprise:

(a) blending the crystalline form of 3-AP together with a controlled-release polymer to form a mixture;
(b) heating said mixture to a temperature sufficient for extrusion of the mixture;
(c) extruding said mixture to form coarse particles having an average diameter ranging from about 0.1 mm to about 5 mm;
(d) cooling said coarse particles; and
(e) processing (e.g., by milling, grinding, or crushing) said coarse particles to form particles having an average diameter less than about 0.1 mm.

In certain embodiments, the particles may have an average diameter ranging from about 0.1 mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns and may be able to pass through a 50 mesh sieve. In certain embodiments, the particles may have a diameter of about 0.1 mm or less.

In certain embodiments, the controlled-release polymer may be heated prior to blending with the crystalline form of 3-AP.

V. Pharmaceutical Compositions (Final Dosage Forms)

The present disclosure further provides pharmaceutical compositions (sometimes referred to as "final dosage forms" or "FDF") comprising compositions according to the present disclosure.

In some embodiments, the pharmaceutical compositions may further comprise at least one excipient (such as, e.g., a controlled-release polymer, surfactant, and/or metal salt), such as a pharmaceutically acceptable excipient. Examples of pharmaceutically acceptable excipients may be, for example, those described in Remington's Pharmaceutical Sciences by E. W. Martin, and include cellulose, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the pharmaceutical compositions also contain pH buffering reagents, and wetting or emulsifying agents.

In some embodiments, the pharmaceutical compositions may be formulated for oral administration. In this embodiment, the pharmaceutical composition may be in the form of, for example, tablets, capsules, or other oral dosage forms. Such oral dosage forms may be prepared by conventional means. The pharmaceutical composition can also be prepared as a liquid, for example as a syrup or a suspension. The liquid can include suspending agents (e.g., sorbitol syrup, cellulose derivatives, or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring, and sweetening agents. Alternatively, the composition can be presented as a dry product for constitution with water or another suitable vehicle.

For buccal and sublingual administration, the composition may take the form of tablets or lozenges according to conventional protocols.

The pharmaceutical composition can also be formulated for rectal administration as a suppository or retention enema, e.g., containing conventional suppository bases such as PEG, cocoa butter, or other glycerides.

In some embodiments, the pharmaceutical compositions described herein provide improved dissolution of the crystalline form of 3-AP, relative to the unencapsulated crystalline form of 3-AP, and/or to another dosage form (such as, e.g., a more invasive dosage form). For example, dissolution may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by a Vankel tablet dissolution apparatus approved by the United States Pharmacopeia.

In some embodiments, the pharmaceutical compositions described herein provide improved oral bioavailability of the crystalline form of 3-AP, relative to the unencapsulated crystalline form of 3-AP, and/or to another dosage form (such as, e.g., a more invasive dosage form). For example, absorption may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are immediate-release formulations. In such embodiments, the pharmaceutical compositions provide a more rapid onset of action of the crystalline form of 3-AP, relative to the unencapsulated crystalline form of 3-AP, and/or to another dosage form (such as, e.g., a more invasive dosage form). For example, the onset of action may be shortened by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are controlled-release formulations. In such embodiments, the pharmaceutical compositions described herein provide a more rapid onset of action of the crystalline form of 3-AP.

In some embodiments, the pharmaceutical compositions described herein have reduced absorption variability, relative to the unencapsulated insoluble drug, and/or to another dosage form (such as, e.g., a more invasive dosage form).

In some embodiments, the pharmaceutical compositions described herein are associated with improved patient compliance, relative to another pharmaceutical composition comprising the crystalline form of 3-AP (which may be in another dosage form, such as, e.g., a more invasive dosage form).

In some embodiments, a pharmaceutical composition of the present disclosure is formulated for oral delivery. Compositions intended for oral use may be prepared in solid or fluid unit dosage forms. In at least some embodiments, the compositions are formulated for oral delivery as tablets, caplets, capsules, pills, powders, troches, elixirs, suspensions, syrups, wafers, chewing gums, dragees, lozenges, and the like.

In some embodiments, the oral dosage forms are solid oral dosage forms such as tablets, caplets, and capsules. In some embodiments, the capsule is a hard capsule or a soft capsule. In other embodiments, the capsule is a gelatin capsule, gelatin-free capsule, a "cap-in-cap" capsule, alginate capsule, hydroxypropylmethyl cellulose (HPMC) capsule, a polyvinyl alcohol (PVA) capsule, a hypromellose capsule, or a starch capsule.

In some embodiments, an oral composition comprising the crystalline form of 3-AP thereof further comprises one or more excipients. In some embodiments, an oral composition comprising the crystalline form of 3-AP or a polymorph thereof further comprises one or more excipients. Accordingly, compositions designed for oral administration can be made with an inert or active excipient or with an edible carrier as disclosed herein.

In various embodiments, the composition provided herein comprises from about 1% to about 99.99%, about 5% to about 95%, about 5% to about 90%, about 10% to about 80%, about 15% to about 70%, about 20% to about 60%, from about 30% to about 95%, from about 50% to about 90%, from about 60% to about 90%, from about 60% to about 80%, or from about 70% to about 80% by weight of one or more excipients. In certain embodiments, the composition provided herein comprises about 99.99%, about 95%, about 90%, about 85%, about 80%, about 75%, about 70%, about 65%, about 60%, about 55%, or about 50% by weight of one or more excipients. In certain embodiments, the composition provided herein comprises about 99.99%, about 99%, about 98%, about 97%, about 96%, about 95%, about 94%, about 93%, about 92%, about 91%, about 90%, about 89%, about 88%, about 87%, about 86%, or about 85% by weight of one or more excipients. In certain embodiments, the composition provided herein comprises about 85%, about 84%, about 83%, about 82%, about 80%, about 79%, about 78%, about 77%, about 76%, about 75%, about 74%, about 73%, about 72%, about 71%, about 70%, about 69%, about 68%, about 67%, about 66%, or about 65% by weight of one or more excipients. In certain embodiments, the composition provided herein comprises about 55%, about 54%, about 53%, about 52%, about 51%, about 50%, about 49%, about 48%, about 47%, about 46%, or about 45% by weight of one or more excipients. In certain embodiments, the composition provided herein comprises about 30%, about 29%, about 28%, about 27%, about 26%, about 25%, about 24%, about 23%, about 22%, about 21%, or about 20% by weight of one or more excipients.

Examples of excipients that can be used in the compositions formulated for oral administration are provided herein and can include, but are not limited to, one or more of bulking agents, binders, fillers, disintegrating agents, lubricants, glidants, control release agents, enteric coatings, film-forming agents, plasticizers, colorants, sweeteners, flavoring agents and the like, or any combination thereof.

Binders suitable for use in the pharmaceutical compositions provided herein include, but are not limited to, sucrose, starches such as corn starch, potato starch, or starches such as starch paste, pregelatinized starch, and starch 1500, PEG 6000, methocel, walocel HM, Luvitec, Luvicaparolactam, Avicel, SMCC, UNIPURE, gelatin, natural and synthetic gums such as acacia, sodium alginate, alginic acid, other alginates, tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, polyvinyl pyrrolidone, hydroxypropyl methyl cellulose, (e.g., Nos 2208, 2906, 2910), microcrystalline cellulose, and mixtures thereof. Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. In some embodiments, the binder is a mixture of microcrystalline cellulose and sodium carboxymethyl cellulose. Suitable anhydrous or low moisture excipients or additives include AVICEL PH 103 and Starch 1500 LM.

Examples of fillers suitable for use in the pharmaceutical compositions provided herein include, but are not limited to, talc, calcium carbonate (e.g., granules or powder), sugars such as dextrose, sucrose, lactose, a salt such as calcium carbonate, calcium phosphate, sodium carbonate, sodium phosphate, starches, microcrystalline cellulose, powdered cellulose, cellulosic bases such as methyl cellulose, carboxymethyl cellulose dextrates, kaolin, mannitol, silicic acid, sorbitol, starch, pregelatinized starch, and mixtures thereof.

One or more binder or filler in compositions is typically present in from about 10% to about 99% (wt/wt) of the composition or the dosage form. In some embodiments, binders and/or fillers in a composition comprise about 15% to 99%, about 20% to 60%, about 25% to 55%, about 30% to 50%, about 35% to 60%, about 50% to 99% (wt/wt) of the composition.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. In some embodiments, the disintegrant is deep in the oral solid dosage form to delay disintegration. The amount of disintegrant used varies based upon the type of formulation, and is readily discernible to those of ordinary skill in the art.

Typical compositions comprise from 0.5% to 15% (wt/wt) of disintegrant. In some embodiments, compositions comprise from 1% to 5% (wt/wt) of disintegrant in the composition. In another embodiment, the disintegrant is 1% to 25%, 2% to 20%, 5% to 15%, 8% to 12%, or about 10% (wt/wt) of the composition.

Disintegrants that can be used in the pharmaceutical compositions provided herein include, but are not limited to, agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, magnesium stearate or potassium stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), Q7-9120 (Dow Corning), and mixtures thereof. If used at all, lubricants are typically used in an amount of less than 1% (wt/wt) of the compositions or dosage forms into which they are incorporated. In yet another embodiment, the lubricant is 0.1% to 3%, such as 0.5% to 1% (wt/wt), of the composition.

Plasticizers may be added to control the softness or pliability of oral dosage forms such as shell of a capsule, caplet or a tablet and thus, may improve the mechanical properties of the pH-sensitive materials of the coatings on the oral dosage forms. Suitable plasticizers, include, without limitation, petroleum oils (for e.g., a paraffinic process oil, a naphthenic process oil, and an aromatic process oil), squalene, squalane, plant oils, (e.g., olive oil, camelia oil, castor oil, tall oil, and a peanut oil), silicon oils, dibasic acid esters, (e.g., dibutyl phthalate, and dioctyl phthalate), liquid rubbers (e.g., polybutene and a liquid isoprene rubber), liquid fatty acid esters (e.g., isopropyl myristate ISM), hexyl laurate, diethyl sebacate, and diisopropyl sebacate, triethyl citrate, triacetin, diethylene glycol, polyethylene glycols, polypropylene glycol, phthalates, sorbitol, glycol salicylate, crotaminton, and glycerin or mixtures thereof. The amount of plasticizer may vary depending upon the chemical composition of the pharmaceutical preparation. In one embodiment, the at least one plasticizer is sorbitol, dimethyl isosorbide, or a glycerol. In another embodiment, the plasticizer is 1% to 10%, such as 3% to 5% (wt/wt), of the composition.

Examples of glidants include, but are not limited to, colloidal silicone dioxide, cellulose, calcium phosphate, di or tri-basic and the like.

As an example of sweeteners or sweetening agents include sucrose, saccharin, dextrose, maltose, sugar substitutes, aspartame, xylitol, mannitol, cyclamate, sucralose, maltitol, sorbitol, acesulfame K and the like.

Examples of flavoring agents include peppermint, methyl salicylate, peppermint, spearment, methyl salicylate, raspberry, red berry, strawberry, pineapple, orange, cherry and the like.

Compositions formulated for oral delivery as disclosed herein, for example, tablets, caplets, and capsules, may be coated with one or more enteric coating agent, control release agent or film forming agent to control or delay disintegration and absorption of the compositions comprising the crystalline form of the compound of Formula I thereof in the gastrointestinal tract and thereby provide a sustained action over a longer period of time. Accordingly, in some embodiments, the tablet can be an enteric tablet, the caplet can be an enteric caplet, or the capsule can be an enteric capsule. The enteric tablets, enteric caplets, or enteric capsules of the present disclosure may be prepared by techniques known in the art.

Pharmaceutical preparations disclosed herein may comprise a control release agent. Examples of control release agent suitable for use include, without limitation, pH-dependent polymers, acid-insoluble polymers, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, waxes, including synthetic waxes, microcrystalline waxes, paraffin wax, carnauba wax, and beeswax; polyethoxylated castor oil derivatives, hydrogenated oils, glyceryl mono-, di-tribenates, glyceryl monostearate, glyceryl distearate, long chain alcohols, such as stearyl alcohol, cetyl alcohol, and polyethylene glycol; and mixtures thereof. In some embodiments, a time delay material such as glyceryl monostearate or glyceryl distearate may be used. In other embodiments, the controlled release reagent is a digestible waxy substance such as hard paraffin wax.

In some embodiments, compositions may comprise one or more of pH-dependent polymers such as acid insoluble polymers. The pH-dependent polymers become increasingly permeable above pH 5.0 but are impermeable at pH below 5.0 whereas acid insoluble polymers become soluble in neutral to weakly alkaline conditions. Such control release polymers target upper small intestines and colon. Non-limiting examples of acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (commercially available under the tradename EUDRAGIT L and EUDRAGIT S from Rohm America Inc., Piscataway, N.J. as a powder or a 30% aqueous dispersion; or under the tradename EASTACRYL, from Eastman Chemical Co., Kingsport, Tenn., as a 30% dispersion). Additional examples include EUDRAGIT L100-55, EUDRAGIT L30D-55, EUDRAGIT L100, EUDRAGIT L100 12,5, EUDRAGIT S100, EUDRAGIT S12,5, EUDRAGIT FS 30D, EUDRAGIT E100, EUDRAGIT E 12,5, and EUDRAGIT PO. In at least one embodiment, the composition comprises EUDRAGIT L100-55. EUDRAGIT RS and RL and EUDRAGIT NE and NM are also useful polymers for the purpose of this disclosure. In some embodiments, the composition comprises EUDRAGIT L30D 55. In another embodiment, the preparation comprises EUDRAGIT FS 30D. One of skill in the art will recognize that at least some acid insoluble polymers listed herein will also be biodegradable.

For time delay or delayed-release pharmaceutical preparations of oral dosage forms, glyceryl monostearate, glyceryl distearate, and acid-insoluble polymers, for example polymethacrylate pH-sensitive polymer-based coatings can be used, (e.g., as coating material, i.e., enteric coating agents, for enteric coating of capsules, caplets, and tablets). Commercial sources for delayed-release oral dosage forms are available, for example DRCaps made of hypromellose (HPMC) from Capsugel, USA. Such delayed-release oral dosage forms are acid-resistant and can resist acidity as seen in stomach for at least 30 minutes, such as for at least 1 hour, for at least 1.5 hour, or for at least 2 hours. Such delayed release oral dosage forms can release at least 40%, at least 50%, at least 60%, at least 70%, at least 80% or at least 90% of the crystalline form of the compound of Formula I thereof in the intestines (small intestines, large intestine/colon etc).

In an aspect of the present disclosure, the enteric tablets, enteric caplets, and enteric capsules may be uncoated. Hard uncoated capsules with enteric capability using intrinsically enteric capsule technology (for example, EnTrinsic Drug Delivery available from Capsugel) are suitable for the purpose of the present disclosure.

In various embodiments, the enteric tablet is a hard tablet made with free-flowing powder of the crystalline form of the compound of Formula I thereof. In various embodiments, the enteric capsule is a capsule made with free-flowing powder of crystalline form of the the compound of Formula I thereof. In various embodiments, the enteric tablet is a hard tablet made with free-flowing powder of the crystalline form of the compound of Formula I. In various embodiments, the enteric capsule is a capsule made with free-flowing powder of the crystalline form of the compound of Formula I.

In some embodiments, the enteric capsule is a non-animal-based capsule, such as a hypromellose capsule (for example, commercially available self-gelling Vcaps, VCaps Plus, VCaps enteric, other enteric capsules made using Xcellodose, ENCODE colonic delivery technology, and EnTrinsic™ drug delivery technology from Capsugel). Other technologies known in the art and available commercially (for example, Qualicaps, USA, Nutrascience, USA, etc.) for the formulating enteric forms of oral solid dosage forms can also be utilized. In at least one embodiment, the capsule is an API-in-capsule, meaning that the crystalline form of the compound of Formula I free base or salts thereof is filled neat into the capsule. In such API-in-capsule oral dosage forms, the active ingredient, the crystalline form of the compound of Formula I can be free flowing powders or micronized powders. When the dosage Form I is a capsule, in at least one embodiment, the capsule can be a seamless capsule or a banded capsule.

Dissolution of the oral dosage forms disclosed herein is tested by the dissolution tests according to the current methods of USP 711. In some embodiments, the oral dosage forms disclosed herein are protected from the acidic environment of the stomach and do not dissolve for at least 2 hours, at least 3 hours, at least 4 hours, at least 5 hours, 6 hours, at least 7 hours or at least 8 hours. In at least one embodiment, the oral dosage forms do not release 3-AP for at least 6 hours. In another embodiment, the oral dosage forms do not release 3-AP for at least 2 hours.

VI. Methods of Making Pharmaceutical Compositions

In further embodiments, the present disclosure provides a method of making a pharmaceutical composition wherein the method further comprises formulating the particulate delivery systems described herein.

In some embodiments, the present disclosure also provides a method of making a pharmaceutical composition wherein the method further comprises mixing the particulate delivery system, wherein said particulate delivery system comprises a first mixture of a compound of Formula I and at least one excipient, with at least one additional excipient to form a second mixture; and formulating the second mixture.

In certain embodiments, the particles are formulated into unit doses such as tablets or capsules.

VII. Methods of Treatment

The pharmaceutical compositions described herein may be useful to treat any disease or condition for which administration of a corresponding insoluble drug is desirable. For example, compositions comprising a crystalline form of the compound of Formula I may be useful for the treatment of cancer. The terms "treat," "treatment," and "treating" refer to (1) a reduction in severity or duration of a disease or condition, (2) the amelioration of one or more symptoms associated with a disease or condition without necessarily curing the disease or condition. In some embodiments, the method of treatment further comprises the prevention of a disease or condition. Suitable subjects include, e.g., humans and other mammals, such as, e.g., mice, rats, dogs, and non-human primates.

In yet another aspect, the disclosure provides a method of treating cancer comprising administering an effective amount of a pharmaceutical composition of the present disclosure to a patient in need thereof.

Other embodiments of the present disclosure will be apparent to those skilled in the art from consideration of the specification and practice of the present disclosure disclosed herein. It is intended that the specification and examples be considered as exemplary only, with the true scope and spirit of the present disclosure.

Examples

Figure 2:
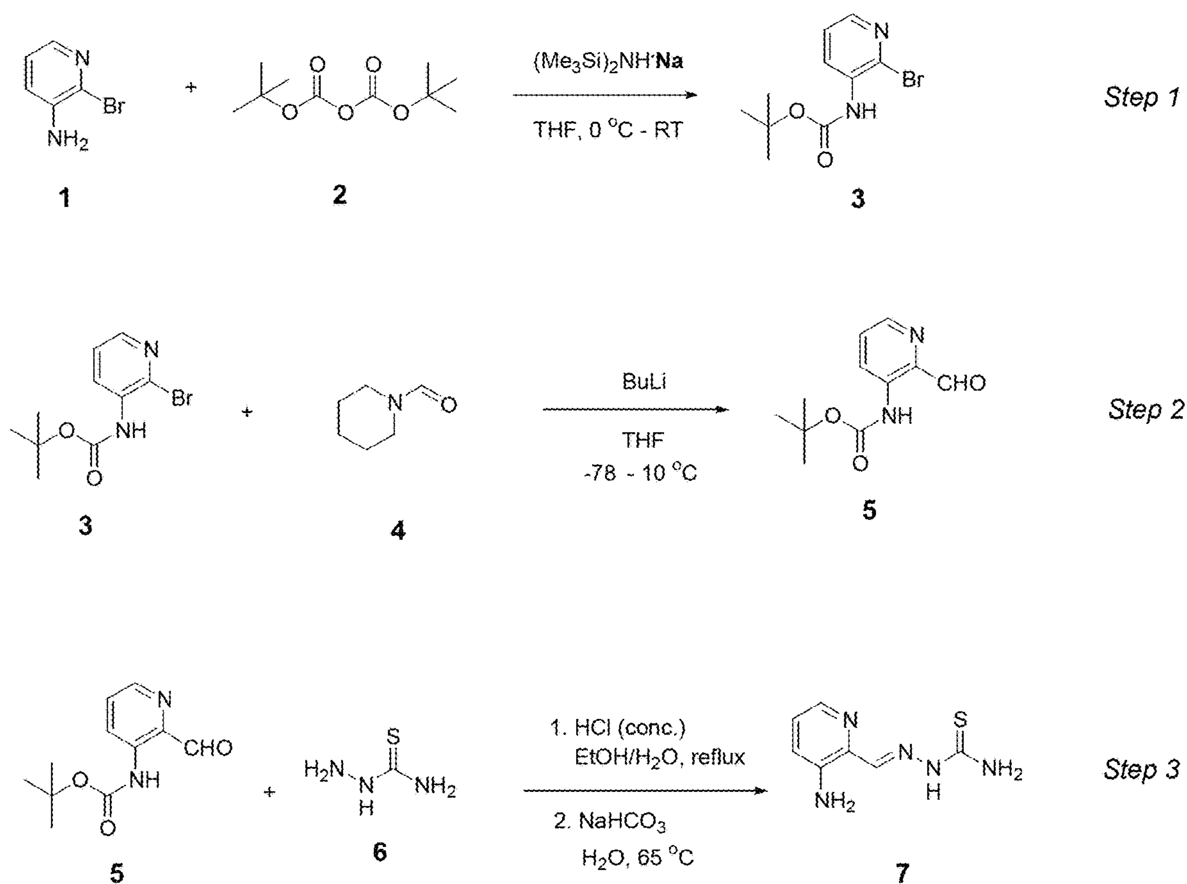
FIG. 2 shows the 3-step synthesis of crystalline fine particle Form I of 3-AP described in Example 1.
Figure 3:
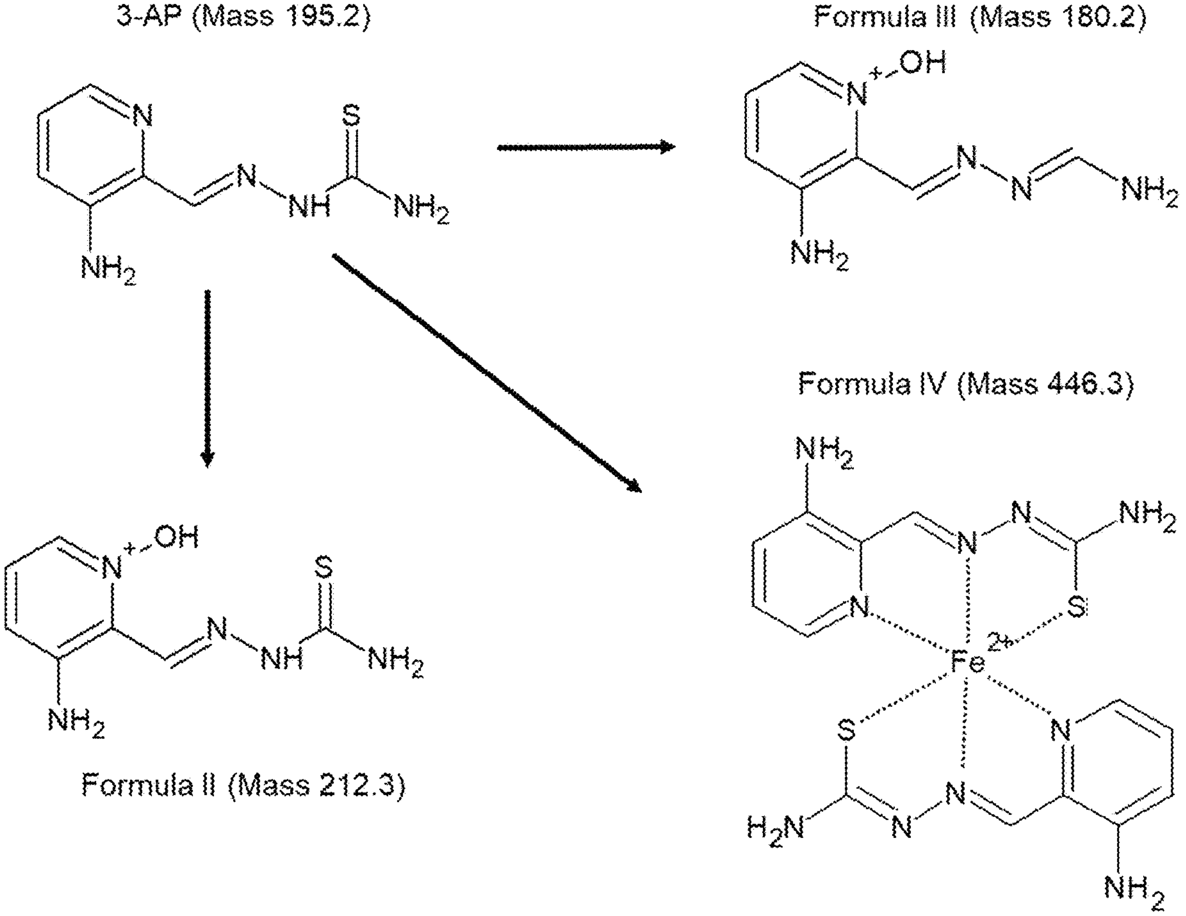
FIG. 3 shows the crystalline fine particle Form I of 3-AP and degradation products having the structure of Formula II: ##STR00002 ##: 3-amino-2-{(E)-[(2E)-(aminomethylidene)hydrazinylidene]methyl}-1-hydroxypyridin-1-ium, and the structure of Formula III: ##STR00003 ##: 3-amino-2-[(E)-(2-carbamothioylhydrazinylidene)methyl]-1-hydroxypyridin-1-ium and compound impurity having the structure of Formula IV: ##STR00004 ##: Fe(II) complex with two 3-AP molecules.

Example 1—Preparation of 400 Erams of Crystalline 3-AP. A novel method for preparing the starting aldehyde 5 for the synthesis of 3-AP was developed. High purity 3-amino-2-bromopyridine (compound 1) is now commercially available reducing the number of required steps. Utilization of this aldehyde 5 in the synthesis of 3-AP (7) at the 400 gram scale is described. The 3-step synthesis scheme is shown in FIG. 2.

Step 1. Boc protection of 3-(tert-Butoxycarbonylamino)-2-bromopyridine (3). Sodium bis(trimethylsilyl) amide (NaHMDS) was used as base for the amino protection. 1M solution of NaHMDS in THF (2.1 equiv.) was added dropwise to a solution of 3-amino-2-bromopyridine compound 1 (1 equiv.) and di-t-butylcarbonate in THF at 0 degrees Celsius. Scale up provided high yield (86-95%) after purification from silica gel plug.

To a solution of 3-amino-2-bromopyridine (197.25 grams, 1.1401 mol) and di-tert-butyl decarbonate (282.6 grams, 1.2948 mol) in anhydrous THF (2 L) in a 12 L three-neck round-bottom flask equipped with a mechanical stirrer was added 1.0 M sodium bis(trimethylsilyl) amide in THF (2.4 L, 2.4 mol) at 1-6 degrees Celsius (internal temperature) over 3 hours under argon. After addition completed, the ice-water bath was removed, and the resulting yellow slurry was stirred at room temperature for 4 hours. The reaction mixture was cooled to 5 degrees Celsius with an ice water bath and quenched with addition of 2N HCl (1.32 L) slowly over 30 min (internal temperature: 5-12 degrees Celsius). The phases were separated, and the organic phase was washed with 50% brine (1 L) and brine (1 L), respectively, dried over $MgSO_4$. Filtration and concentration provided 410 grams crude intermediate as yellow solid, which was dissolved in $CH_2Cl_2$ (150 mL). The solution was loaded to a pre-wetted with 10% EtOAc/Heptane silica gel plug (956 grams) and eluted with 10% EtOAc/Heptanes (7 L) to obtain 622.9 g of 3-(tert-Butoxycarbonylamino)-2-bromopyridine (3) obtained in 85.7% yield. Batch #: AL1024-33. 1H NMR (300 MHz, $CDCl_3$) δ 8.44 (dd, J=7.8, 1.5 Hz 1H), 8.01 (dd, J=4.2, 1.8 Hz, 1H), 7.23 (dd, J=8.1, 4.5 Hz, 1H), 7.02 (br s, 1H), 1.53 (s, 9H).

Step 2. Synthesis of aldehyde 3-(N-tert-Butoxycarbonylamino)-2-pyridinecarboxaldehyde (5). Treatment of the tert-Boc protected 3-amino-2-bromopyridine 3 with n-BuLi in anhydrous THF resulted in the lithiated species, which was further reacted with N-formylpiperidine to give the carboxaldehyde 5. This reaction was performed at low temperature (−65 to −70 degrees Celsius). Treatment with sodium bisulfite, aldehyde 5 was obtained in 74% yield with 99.3% HPLC purity avoiding the need for chromatography purification previously described.

n-Butyl solution in hexanes (1.6 M, 4243 mL, 6.7888 mol) was added dropwise to a solution of starting bromide (883 g, 3.2328 mol) in anhydrous THF (4250 mL) in a 20 L three-neck round-bottom flask equipped with a mechanical stirrer using a dry ice cooling bath at −72 to −68 degrees Celsius (internal temperature) over 3 hours under argon. The resulting yellow mixture was stirred at the same temperature for 1 hour. Then 1-formylpiperidine (548.8 g, 1.8857 mol) was added dropwise over 0.5 hour using a dry ice cooling bath at −72 to −65 degrees Celsius (internal temperature). The dry ice cooling bath was replaced by an ice-water bath, and the reaction mixture was warmed to 0 degrees Celsius over 35 minutes, then stirred at this temperature for 1 hour. The reaction mixture was then quenched with drop-wise addition of 2N HCl (5274 mL) below 6 degrees Celsius over 50 minutes. The pH was adjusted to 7 by addition of solid sodium carbonate (120.1 grams). The organic layer was separated, and the aqueous layer was extracted with ethyl acetate (3×5.2 L). The combined organic phases were washed with water (2×5.3 L), brine (5.3 L), and dried over magnesium sulfate overnight. Filtration and concentration provided 939 g of crude product as yellow wax. This residue was dissolved in ethyl acetate (6320 mL) and was added to a solution of sodium bisulfite (403.3 grams, 3.8779 mol) in water (843 mL). The mixture was stirred at room temperature overnight. The resulting white slurry was filtered, and the solid was washed with ethyl acetate (2×1077 mL), to provide 1244 g of sodium salt as wet off-white solid. This solid was suspended in ethyl acetate (6320 mL) and treated with a solution of sodium hydroxide (210.8 grams) in water (1055 mL) until the solid completely dissolved (1 hour). The phases were separated, and the aqueous phase was extracted with ethyl acetate (2×1055 mL). The combined organic phases were washed with brine (1055 mL), dried over $MgSO_4$ for 1 hour. Filtration and concentration provided 533 grams of product as light-yellow solid in 74.2% yield. Batch #: AL1024-35. HPLC: 99.3%%. $^1H$ NMR (300 MHz, $CDCl_3$) δ 10.21 (s, 1H), 10.07 (s, 1H), 8.83 (d, J=8.7 Hz, 1H), 8.40 (dd, J=4.2, 1.2 Hz, 1H), 7.45 (dd, J=8.7, 4.2 Hz, 1H), 1.53 (s, 9H). 13C NMR (75 MHz, CDCl3) δ 197.1, 152.7, 143.2, 139.2, 136.6, 128.6, 126.2, 81.6, 28.1.

Step 3. Synthesis of 3-AP (7). The condensation reaction of aldehyde 5 with thiosemicarbazide (6) in ethanol and water in the presence of concentrated HCl and deprotection afforded 3-AP hydrochloride, which was converted into the free base by basification with sodium bicarbonate solution under cGMP conditions. High yield (91.74%) and purity (99.92%) have been obtained.

A mixture of starting aldehyde (533 g, 2.3983 mol) and thiosemicarbazide (238.4 g, 2.6157 mol) in ethanol/water (5440 mL/2720 mL, ethanol:water=2:1) was stirred in 20-L flask at room temperature under argon for 0.5 hour. A light yellow slurry formed. Concentrated hydrochloric acid (1094 mL) was added dropwise to the above mixture below 30 degrees Celsius. The resulting yellow slurry was heated to reflux for 3 hours. The heating bath was removed, and the mixture was cooled spontaneously to room temperature, then cooled with ice-water bath to 5 degrees Celsius for 1 hour. The solid was filtered, washed with cold water (2×1120 mL) to provide 870 g yellow solid. This solid was suspended in water (14.95 L) in a 20-L flask and heated to 70-80 degrees Celsius for 20 minutes. The resulting cloudy solution was hot filtered (to remove insoluble materials) through 3-L fritted filter and the flask was rinsed with water 3 times (3×280 mL). The clear 3-AP HCl solution was transferred into 50-L reactor under argon atmosphere. Sodium bicarbonate solution (496 g $NaHCO_3$ in 4960 mL water) was added dropwise with vigorously stirring while maintaining the temperature of mixture at 45-65 degrees Celsius. The resulting yellow suspension was cooled to room temperature overnight for crystallization, then cooled to 1-5 degrees Celsius for 1 hour. The crystalline solid was filtered, washed with cold water (2×3730 mL), ethanol (1066 mL), and diethyl ether (3730 mL), then dried in a vacuum oven under high vacuum (29.37 inch) at 40 degrees Celsius for 18.5 hours to obtain 427 g crystalline 3-AP as a yellow solid (yield: 91.74%). HPLC: 99.92%. $^1H$ NMR (300 MHz, DMSO-d6) δ 11.28 (s, 1H), 8.31 (s, 1H), 8.14 (br s, 1H), 7.94 (br s, 1H), 7.81 (d, J=3.9 Hz, 1H), 7.12 (d, J=8.4, 1H), 7.04 (dd, J=8.4, 4.2 Hz, 1H), 6.42 (s, 2H).

This new method has been scaled to 400 gram scale for the synthesis of 3-(N-tert-butoxycarbonylamino)-2-pyridinecarboxaldehyde (5), the major starting material for the preparation of 3-AP (7). This three step process eliminated the chromatography purification reported in the literature and U.S. Pat. No. 5,869,676. The utilization of this aldehyde to synthesis of 3-AP for 400 gram scale has also been demonstrated and high HPLC purity (99.92%) was obtained.

Figure 5:
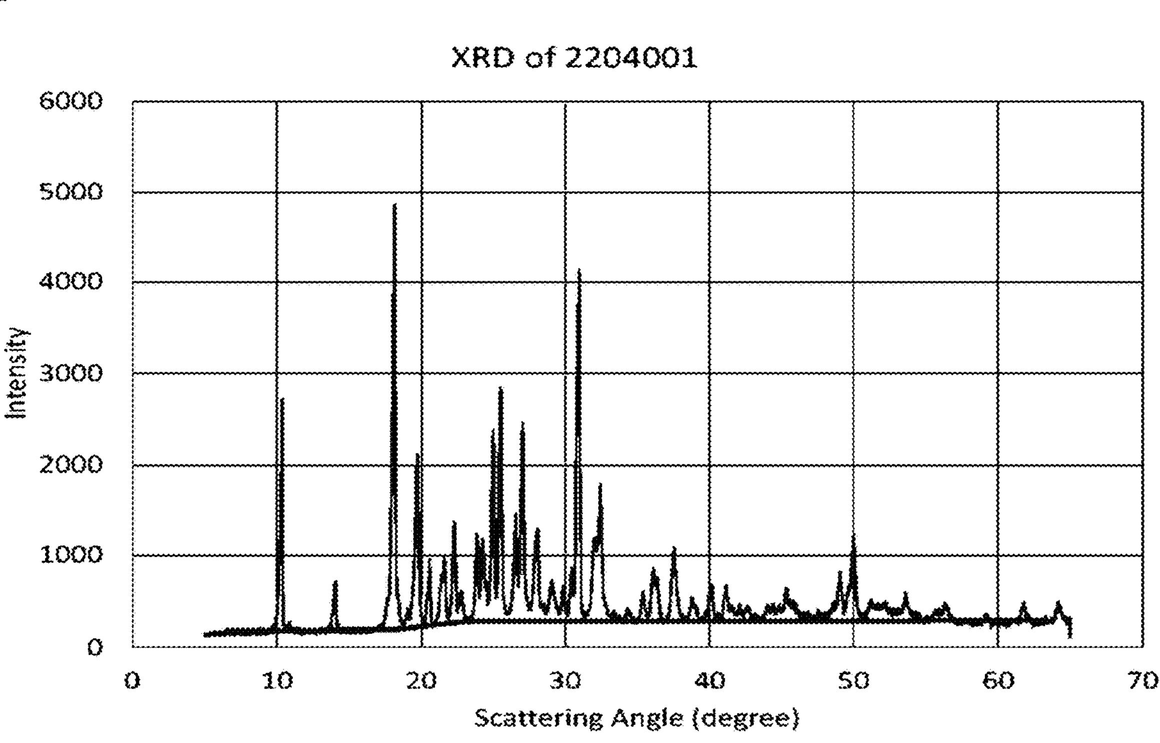
FIG. 5 is the XRD pattern of Example 2 (A) crystalline fine particle Form I of 3-AP scale-up batch Lot NC2204001 and (B) 15% NC2204001 was mixed with 85% Starch 1500 by weight.
Figure 5:
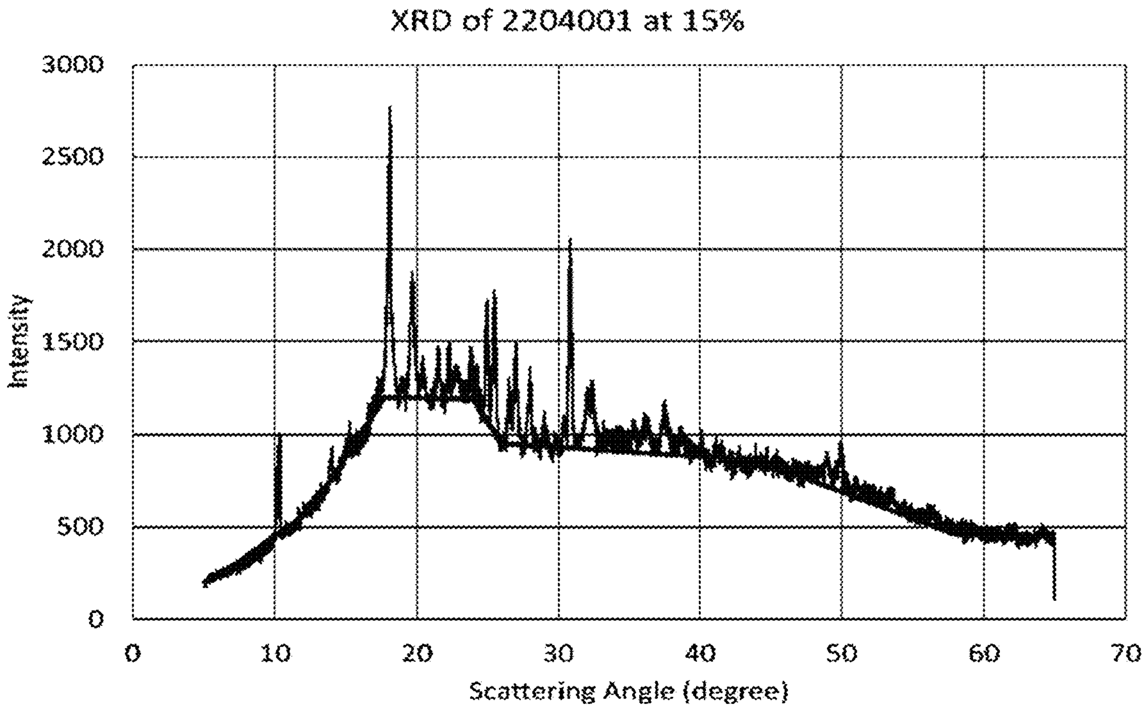

Example 2—X-ray Diffraction of Crystalline 3-AP. Crystalline fine particle Form I of 3-AP samples of Examples 1 (NC2204001 and NC2205002) 400 gram batches and earlier batches (NC2201001, 200 g) were used to identify differences in the crystalline structure of the three samples through standard x-ray diffraction (XRD) measurement. In both examples the same peaks were obtained, shown in FIG. 4A to 5B as well as Tables 1 to 4, respectively. In FIG. 5B and Table 4, 15% NC2204001 was mixed with 85% Starch 1500 by weight similar to the oral capsule formulation in Example 8 to demonstrate the crystal structure is preserved in oral preparations.

TABLE 1

XRD of NC2201001 (FIG. 4A)

| Peak Value (degree) | Intensity | Intensity - baseline |
|---|---|---|
| 10.36296 | 3053 | 2883.9 |
| 10.88101 | 305 | 135.5 |
| 14.05615 | 643 | 471.0 |
| 18.1337 | 4644 | 4467.7 |
| 19.11967 | 393 | 207.3 |
| 19.75469 | 1932 | 1740.2 |
| 20.55684 | 1052 | 852.5 |
| 21.62636 | 840 | 630.2 |
| 22.34494 | 999 | 782.4 |
| 22.71259 | 470 | 249.8 |
| 23.93251 | 680 | 448.1 |
| 24.35029 | 860 | 624.1 |
| 25.01874 | 1490 | 1247.7 |
| 25.55351 | 1754 | 1506.6 |
| 26.60632 | 925 | 667.5 |
| 27.07423 | 1510 | 1248.0 |
| 28.04348 | 1010 | 738.7 |
| 28.46127 | 511 | 235.7 |
| 29.12972 | 654 | 372.3 |
| 29.91515 | 522 | 232.8 |
| 30.4332 | 782 | 492.1 |
| 30.91782 | 5055 | 4765.2 |
| 32.104 | 1200 | 910.5 |
| 32.42184 | 1708 | 1418.6 |
| 33.30753 | 381 | 91.8 |
| 35.37973 | 493 | 204.3 |
| 36.11503 | 725 | 436.5 |
| 36.33227 | 665 | 376.6 |
| 37.51877 | 1148 | 859.9 |
| 38.77212 | 437 | 149.2 |
| 40.10902 | 574 | 286.5 |
| 40.57694 | 358 | 70.6 |
| 41.16183 | 729 | 441.8 |
| 41.5629 | 513 | 225.9 |
| 42.09766 | 380 | 93.0 |
| 42.73269 | 436 | 149.2 |
| 44.06959 | 411 | 124.5 |
| 44.42053 | 444 | 157.6 |
| 44.83831 | 391 | 104.7 |
| 45.37307 | 557 | 270.8 |
| 45.92454 | 459 | 173.0 |
| 47.61238 | 343 | 57.4 |
| 48.46465 | 403 | 117.6 |
| 49.04955 | 805 | 519.8 |
| 49.98538 | 1317 | 1032.0 |
| 51.17188 | 445 | 160.3 |
| 51.65651 | 400 | 115.4 |
| 51.92389 | 373 | 88.5 |
| 52.22469 | 390 | 105.6 |
| 52.64247 | 399 | 114.7 |
| 53.19394 | 353 | 68.8 |
| 53.61173 | 528 | 243.9 |
| 55.70063 | 380 | 96.4 |
| 56.3858 | 451 | 167.6 |
| 59.21 | 343 | 60.3 |

TABLE 1-continued

XRD of NC2201001 (FIG. 4A)

| Peak Value (degree) | Intensity | Intensity - baseline |
|---|---|---|
| 61.78354 | 457 | 174.9 |
| 64.18996 | 538 | 256.5 |

TABLE 2

XRD of NC2205002 (FIG. 4B)

| Peak Value (degree) | Intensity | Intensity - baseline |
|---|---|---|
| 10.36296 | 2410 | 2224.1 |
| 10.89772 | 305 | 116.0 |
| 14.05615 | 935 | 727.8 |
| 18.1337 | 4731 | 4498.9 |
| 19.05282 | 431 | 184.2 |
| 19.72127 | 2549 | 2291.5 |
| 20.57355 | 824 | 552.8 |
| 21.62636 | 1119 | 831.0 |
| 22.34494 | 1377 | 1077.5 |
| 22.86299 | 624 | 316.2 |
| 23.93251 | 1581 | 1271.0 |
| 24.334 | 1245 | 935.0 |
| 25.01874 | 2804 | 2494.0 |
| 25.53679 | 3431 | 3121.0 |
| 26.57289 | 1700 | 1390.0 |
| 27.05752 | 2886 | 2576.0 |
| 28.0602 | 1432 | 1122.0 |
| 29.07958 | 820 | 510.0 |
| 29.88172 | 845 | 535.0 |
| 30.46662 | 868 | 558.0 |
| 30.951 | 3945 | 3635.0 |
| 32.0709 | 1126 | 816.0 |
| 32.43855 | 1701 | 1391.0 |
| 33.34096 | 366 | 56.0 |
| 34.37706 | 430 | 120.0 |
| 35.37973 | 691 | 381.0 |
| 36.09832 | 806 | 496.0 |
| 36.34898 | 767 | 457.0 |
| 37.53549 | 1126 | 816.0 |
| 38.78883 | 580 | 270.0 |
| 40.10902 | 740 | 430.0 |
| 40.54351 | 371 | 61.0 |
| 41.14512 | 717 | 407.0 |
| 41.54619 | 586 | 276.0 |
| 42.11437 | 523 | 213.0 |
| 42.71598 | 480 | 170.0 |
| 43.26745 | 386 | 76.0 |
| 44.0863 | 469 | 159.0 |
| 44.42053 | 522 | 212.0 |
| 44.78818 | 471 | 161.0 |
| 45.37307 | 620 | 310.0 |
| 45.79085 | 465 | 155.0 |
| 45.84099 | 482 | 172.0 |
| 46.39246 | 380 | 70.0 |
| 46.81024 | 399 | 89.0 |
| 47.67923 | 382 | 72.0 |
| 47.91318 | 391 | 81.0 |
| 48.09701 | 379 | 69.0 |
| 48.51479 | 459 | 149.0 |
| 49.04955 | 889 | 579.0 |
| 49.98538 | 1206 | 896.0 |
| 51.13846 | 502 | 192.0 |
| 51.62308 | 528 | 218.0 |
| 52.19127 | 546 | 236.0 |
| 52.49207 | 459 | 149.0 |
| 52.80958 | 453 | 143.0 |
| 53.04354 | 434 | 124.0 |
| 53.61173 | 545 | 235.0 |
| 54.26347 | 405 | 95.0 |
| 54.464 | 393 | 83.0 |
| 55.75077 | 466 | 156.0 |
| 56.36909 | 519 | 209.0 |

TABLE 2-continued

| XRD of NC2205002 (FIG. 4B) | | |
|---|---|---|
| Peak Value (degree) | Intensity | Intensity - baseline |
| 61.78354 | 543 | 233.0 |
| 64.22338 | 479 | 169.0 |

TABLE 3

| XRD of NC2204001 (FIG. 5A) | | |
|---|---|---|
| Peak Value (degree) | Intensity | Intensity - baseline |
| 10.36296 | 2410 | 2194.8 |
| 10.8643 | 305 | 85.8 |
| 14.05615 | 935 | 692.1 |
| 18.1337 | 4731 | 4457.5 |
| 19.06953 | 431 | 150.6 |
| 19.73798 | 2549 | 2263.6 |
| 20.57355 | 824 | 532.2 |
| 21.64307 | 1119 | 819.3 |
| 22.34494 | 1377 | 1071.9 |
| 22.82957 | 624 | 315.0 |
| 23.93251 | 1581 | 1271.0 |
| 24.31687 | 1245 | 935.0 |
| 25.01874 | 2804 | 2494.0 |
| 25.53679 | 3431 | 3121.0 |
| 26.57289 | 1700 | 1390.0 |
| 27.05752 | 2886 | 2576.0 |
| 28.0602 | 1432 | 1122.0 |
| 28.42784 | 820 | 510.0 |
| 29.09629 | 845 | 535.0 |
| 29.88172 | 868 | 558.0 |
| 30.46662 | 3945 | 3635.0 |
| 30.93453 | 1126 | 816.0 |
| 32.03748 | 1701 | 1391.0 |
| 32.43855 | 366 | 56.0 |
| 33.34096 | 430 | 120.0 |
| 34.36034 | 691 | 381.0 |
| 35.39644 | 806 | 496.0 |
| 36.0816 | 767 | 457.0 |
| 36.33227 | 1126 | 816.0 |
| 37.53549 | 580 | 270.0 |
| 38.82225 | 740 | 430.0 |
| 40.09231 | 371 | 61.0 |
| 41.14512 | 717 | 407.0 |
| 41.51277 | 586 | 276.0 |
| 42.09766 | 523 | 213.0 |
| 42.68256 | 480 | 170.0 |
| 44.05288 | 386 | 76.0 |
| 44.43724 | 471 | 188.5 |
| 44.87173 | 417 | 134.4 |
| 45.37307 | 612 | 329.2 |
| 45.80756 | 500 | 217.0 |
| 46.79353 | 358 | 74.7 |
| 47.26144 | 346 | 62.5 |
| 47.62909 | 365 | 81.4 |
| 47.69594 | 366 | 82.4 |
| 48.11372 | 377 | 93.2 |
| 49.04955 | 808 | 523.9 |
| 49.98538 | 1215 | 930.6 |
| 51.18859 | 473 | 188.2 |
| 51.67322 | 455 | 170.0 |
| 51.90718 | 436 | 150.9 |
| 52.17456 | 473 | 187.8 |
| 52.5422 | 393 | 107.7 |
| 52.80958 | 400 | 114.6 |
| 52.99341 | 400 | 114.5 |
| 53.59501 | 571 | 285.3 |
| 54.33031 | 364 | 78.1 |
| 55.11574 | 337 | 50.8 |
| 55.75077 | 373 | 86.6 |
| 56.01815 | 389 | 102.5 |
| 56.35237 | 430 | 143.4 |
| 59.19329 | 350 | 62.4 |

TABLE 3-continued

| XRD of NC2204001 (FIG. 5A) | | |
|---|---|---|
| Peak Value (degree) | Intensity | Intensity - baseline |
| 61.81696 | 486 | 197.5 |
| 63.3544 | 343 | 53.9 |
| 64.20667 | 469 | 179.6 |

TABLE 4

| XRD of NC2204001 15% in Starch 1500 (FIG. 5B) | | |
|---|---|---|
| Peak Value (degree) | Intensity | Intensity - baseline |
| 10.31283 | 948 | 481.1 |
| 14.00602 | 920 | 157.2 |
| 15.05883 | 974 | 88.2 |
| 16.96391 | 1183 | 74.8 |
| 17.248 | 1310 | 168.6 |
| 18.10028 | 2727 | 1527.6 |
| 19.03611 | 1268 | 70.1 |
| 19.70456 | 1863 | 666.1 |
| 20.45657 | 1332 | 136.3 |
| 21.57622 | 1416 | 222.1 |
| 22.29481 | 1455 | 262.3 |
| 22.89641 | 1295 | 103.2 |
| 23.34762 | 1290 | 99.0 |
| 23.86567 | 1456 | 265.8 |
| 24.26674 | 1283 | 125.0 |
| 24.98532 | 1702 | 630.2 |
| 25.52008 | 1748 | 740.4 |
| 26.55618 | 1301 | 353.8 |
| 27.0241 | 1492 | 547.1 |
| 28.02677 | 1361 | 421.1 |
| 29.04616 | 1036 | 101.2 |
| 29.83159 | 1004 | 73.2 |
| 30.85098 | 2057 | 1131.3 |
| 32.03748 | 1250 | 330.2 |
| 32.38841 | 1293 | 374.9 |
| 32.8062 | 1019 | 103.0 |
| 33.15713 | 1073 | 158.8 |
| 33.62505 | 1018 | 106.1 |
| 34.41048 | 1039 | 131.1 |
| 34.82826 | 1014 | 108.1 |
| 35.31289 | 1038 | 134.6 |
| 36.0816 | 1076 | 176.4 |
| 36.33227 | 1006 | 107.7 |
| 37.48535 | 1134 | 241.4 |
| 38.72199 | 1004 | 117.6 |
| 40.0756 | 979 | 99.4 |
| 41.1117 | 953 | 78.6 |
| 46.82695 | 851 | 71.8 |
| 48.99942 | 860 | 142.8 |
| 49.93525 | 924 | 233.6 |
| 51.85704 | 728 | 92.5 |
| 52.19127 | 712 | 86.0 |
| 53.59501 | 666 | 80.1 |
| 54.89849 | 624 | 75.4 |
| 55.48339 | 603 | 71.1 |
| 56.068 | 620 | 104.8 |
| 56.93727 | 563 | 72.6 |
| 57.37176 | 555 | 77.1 |
| 58.50813 | 537 | 77.4 |
| 59.09302 | 530 | 70.9 |

Example 3—Crystalline Fine Particle 3-AP Forced Degradation Study. Crystalline fine particle Form I of 3-AP was subjected to a forced degradation study using acid, base, or hydrogen peroxide exposure for 24-48 hours. Samples were neutralized and analyzed using LC-UV-MS. Table 5 lists the LC-UV-MS conditions.

TABLE 5

| LC-UV-MS conditions | |
|---|---|
| HPLC/MS | Agilent LC/MSD 6120B |
| Source | Electrospray (ESI) |
| Ionization Mode | Positive Ion |
| Method | Gradient Conditions |
| Mobile Phase A | Water with 20 mM Ammonium Acetate |
| Mobile Phase B | 90/20 Acetonitrile/Water with 20 mM Ammonium Acetate |
| Gradient (long) | 90/10 A/B (0 min) -> 90/10 A/B (2 min) -> 10/90 A/B (30 min) -> 10/90 A/B (35 min) -> 90/10 A/B (36.0 min) -> 90/10 A/B (40 min) |
| Gradient (short) | 90/10 A/B (0 min) -> 90/10 A/B (2 min) -> 50/50 A/B (16 min) -> 50/50 A/B (18 min) -> 90/10 A/B (19.0 min) -> 90/10 A/B (25 min) |
| Column | Thermo Synchronis aQ C18 Polar Endcapped 250 x 4.6 mm 5 um SN#13768 |
| Temp | 30° C. |
| Flow Rate | 1 mL/min |
| Injection Volume | 10 uL |
| Scan | 75 to 1000 m/z |
| Step Size | 0.1 m/z |
| Fragmentor | 110 V |
| Gain | 15 |
| Threshold | 100 |
| Drying Gas | 325 degrees Celsius |
| Capillary | 3000 V |
| Nebulizer Gas | 7 LPM |

Sample Preparation: Solid-state stability was tested by exposing 100 mg of crystalline fine particle Form I of 3-AP to light/UV (5 days) and heat (70 degrees Celsius for 5 days). Solution stability was tested with crystalline fine particle Form I of 3-AP, 50 mg, weighed out into a 25 mL volumetric flask and taken to volume with methanol (2 mg/mL stock) and diluted further, 1:10 with 20/80 methanol/water for a final concentration of 0.2 mg/mL. One mL of either 1N and 12N HCl (acid), 1N NaOH (base), and 3% $H_2O_2$ (peroxide) was added to the appropriate vial and mixed, followed by storage at different temperatures. After storage, the samples of acid and base were neutralized by addition of 1 mL their counter solution and 1 mL of water was added to the peroxide samples. Samples were analyzed using LC-UV-MS.

Table 6 lists a comparison for the control, UV (light for 5 days), heat (70 degrees Celsius for 5 days), acid (1N and 12N HCl), base (1N NaOH), and peroxide (3% $H_2O_2$) samples showing impurities by relative retention time (RRT) at 220 nm. While some minor changes can be noted between the control with the UV and heated samples, the overall purity (peak area) of the parent molecule is just slightly higher. The greatest change in purity was noted in the strong acid and $H_2O_2$ samples.

TABLE 6

3-AP Forced Degradation Study

| | Purity | RRT 0.31 | RRT 0.42 | RRT 0.87 II | RRT 0.97 | RRT 1.01 | RRT 1.05 | RRT 1.32 III | RRT 1.60 |
|---|---|---|---|---|---|---|---|---|---|
| Control | 98.5% | | | | | | | | |
| UV exposure (powder) | 99.0% | | | | X | | | | |
| Heated 70 C. (powder) | 99.8% | | | | | | | | |
| Base (weak 1N NaOH) | 93.4% | | | X | X | | | X | |
| Acid (1N HCl) | 79.8% | | | X | X | | | X | X |
| Strong Acid (12N HCl) | 22.1% | | | | X | | | X | X |
| Peroxide (3% H2O2) | 1.2% | X | X | X | | X | | | |

Figure 6:
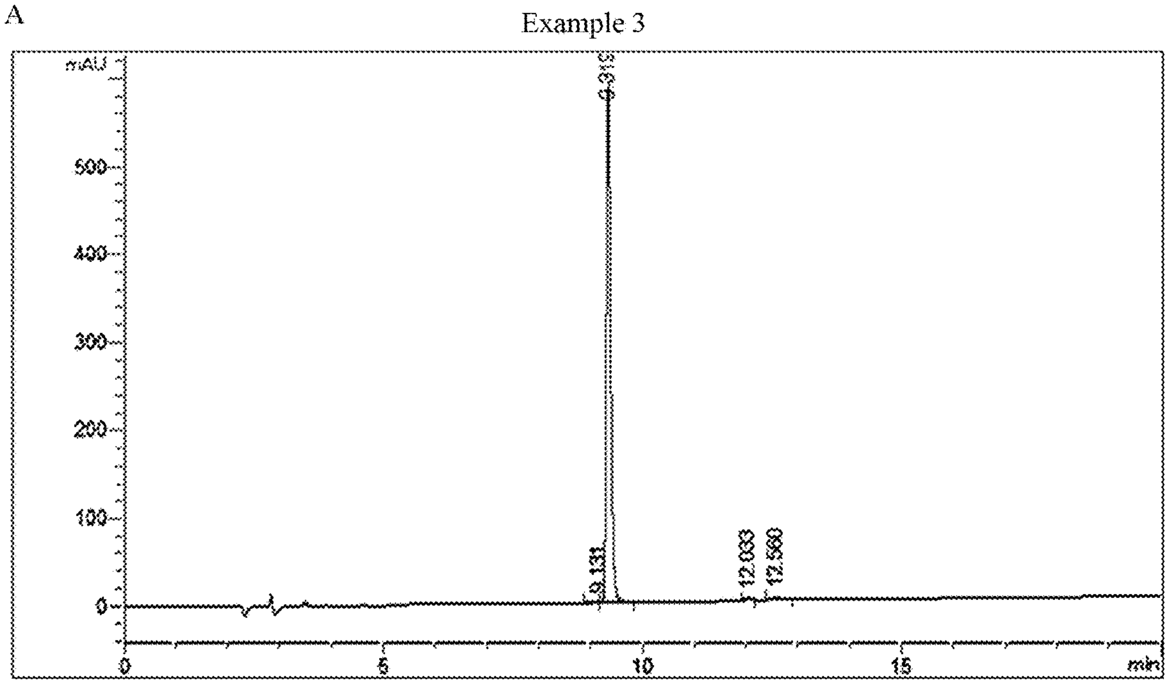
FIG. 6 shows the crystalline fine particle Form I of 3-AP (A) HPLC chromatogram at 220 nm and (B) UV-Vis spectra at RRT 1.0 (9.3 minutes) showing the characteristic 360 nm 3-AP peak.
Figure 6:
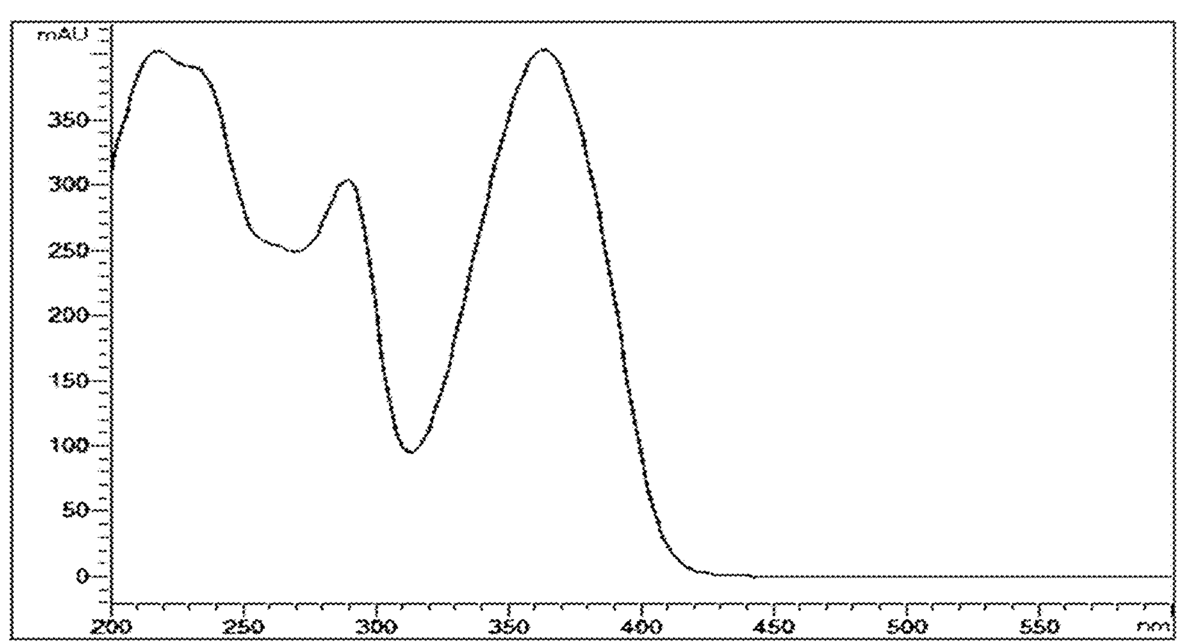

Control Sample: Based on the purity peak area at 220 nm, the control was 98.5%. The HPLC chromatogram at 220 nm is shown in FIG. 6A and UV spectra at RRT 1.0 (9.3 minutes) showing the characteristic 360 nm 3-AP peak in FIG. 6B (also referenced in FIG. 4*a*, Plamthottam-2019).

UV Exposure Sample: Based on the purity peak area at 220 nm, the control was 98.5% and the UV sample was 99.0% with one minor degradant at RRT 0.97 peak as 0.2%.

Heat 70 C Sample: Based on the purity peak area at 220 nm, the control was 98.5% and the heated sample was 99.8%.

Base Degradation Sample: Based on the purity peak area at 220 nm, the control was 98.5% and the Base Degradation (weak 1N NaOH) sample was 93.4% with minor degradants at RRT 0.87 (1.9%), 0.97 (1.9%), 1.18 (2.0%), 1.29 (0.5%), and 1.32 (0.3%).

Figure 7:
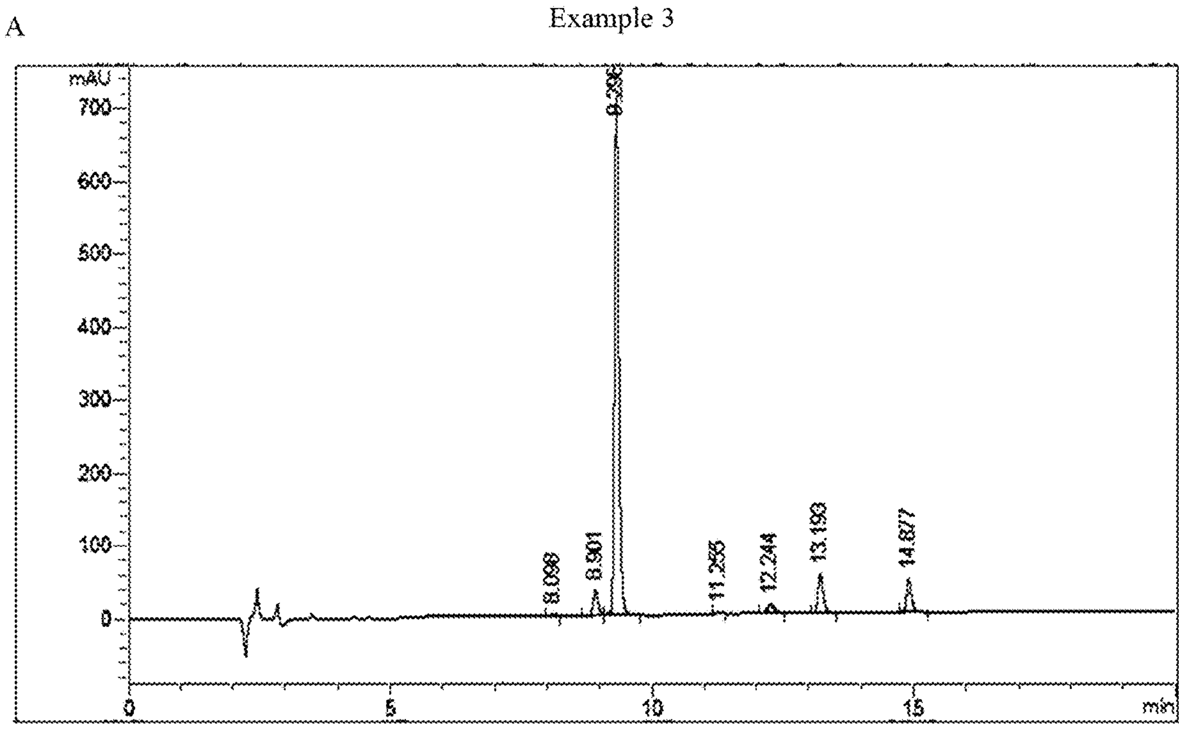
FIG. 7 is the Example 3 crystalline fine particle Form I of 3-AP forced degradation sample in Acid (1N HCl) showing (A) the HPLC chromatogram at 220 nm with 6 degradants at RRT 0.87 (0.4%), 0.97 (4.6%), 1.21 (0.2%), 1.32 (2.0%), 1.42 (7.2%), and 1.60 (5.7%), and (B) UV spectra of the 8.9 minute peak (RRT 0.96) showing a reduction in the characteristic 360 nm 3-AP peak.
Figure 7:
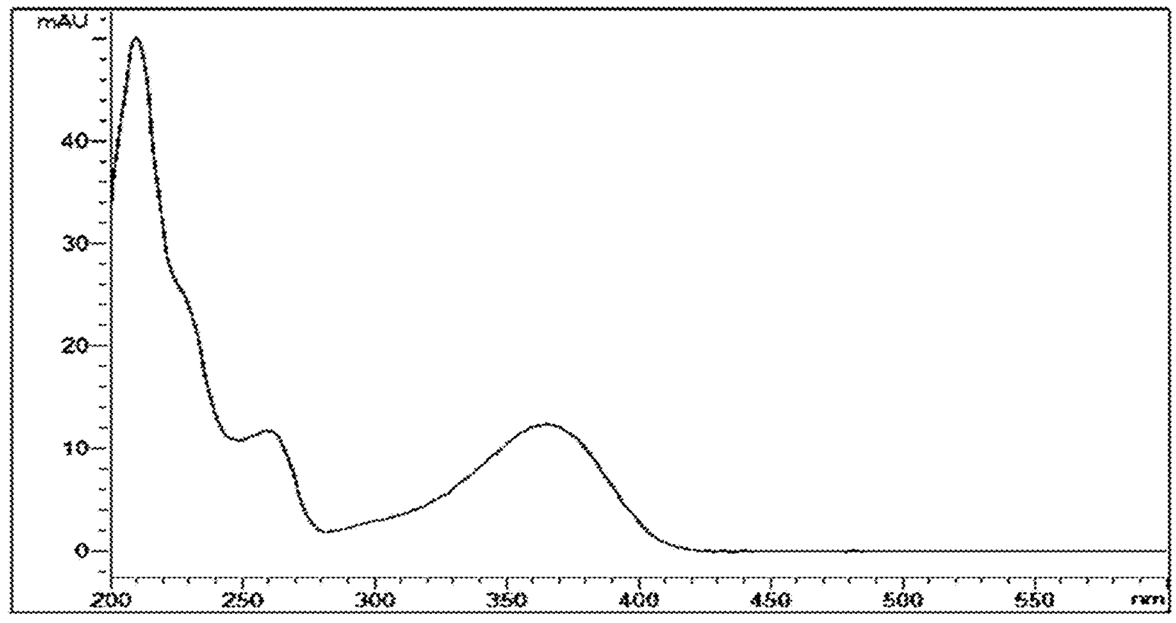

Acid (1N HCl) Degradation Sample: Based on the purity peak area at 220 nm, the control was 98.5% and the Acid Degradation (weak 1N HCl) sample was 79.8% (FIG. 7A). 1N HCl for 5 days reacted with 3-AP and formed 6 degradants at RRT 0.87 (0.4%), 0.97 (4.6%), 1.21 (0.2%), 1.32 (2.0%), 1.42 (7.2%), and 1.60 (5.7%). The UV spectra of the 8.9 minute peak showing a reduction in the characteristic 360 nm 3-AP peak (RRT 0.96) is shown in FIG. 7B.

Figure 8:
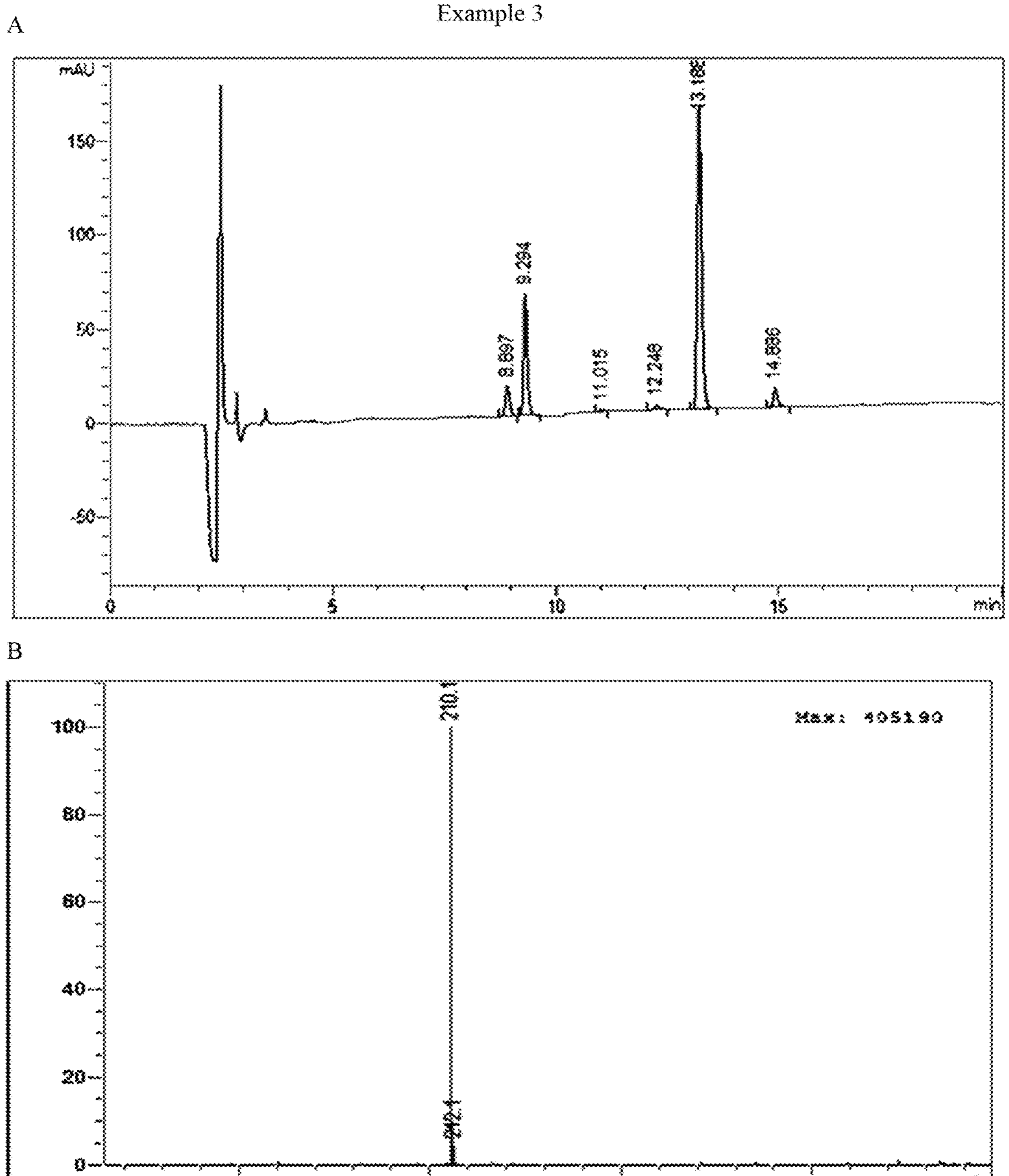
FIG. 8 is the Example 3 crystalline fine particle Form I of 3-AP forced degradation sample in Strong Acid (12N HCl) showing (A) the HPLC chromatogram at 220 nm with 5 degradants with the largest at RRT 1.42 peak as 65.3% and (B) mass spectra of the major degradant peak at RRT 1.42 with 210.1 m/z is Formula II: ##STR00002 ##: 3-amino-2-{(E)-[(2E)-(aminomethylidene)hydrazinylidene]methyl}-1-hydroxypyridin-1-ium.

Strong Acid (12N HCl) Degradation Sample: Based on the purity peak area at 220 nm, the control was 98.5% and the Strong Acid (12N HCl) sample was 22.1%, 12N HCl for 2 days reacted with 3-AP and formed 5 degradants with the largest at RRT 1.42 peak as 65.3%, with other peaks at RRT 0.97 (6.5%), 1.19 (0.4%), 1.32 (1.4%), and 1.60 (4.3%). The HPLC chromatogram at 220 nm is shown in FIG. 8A and MS spectra of the major degradant peak at RRT 1.42 (13.2 minutes) is shown in FIG. 8B. The proposed structure of the major degradant peak at RRT 1.42 with 210.1 m/z is Formula II: 3-amino-2-{(E)-[(2E)-(aminomethylidene)hydrazinylidene]methyl}-1-hydroxypyridin-1-ium (FIG. 1).

Figure 9:
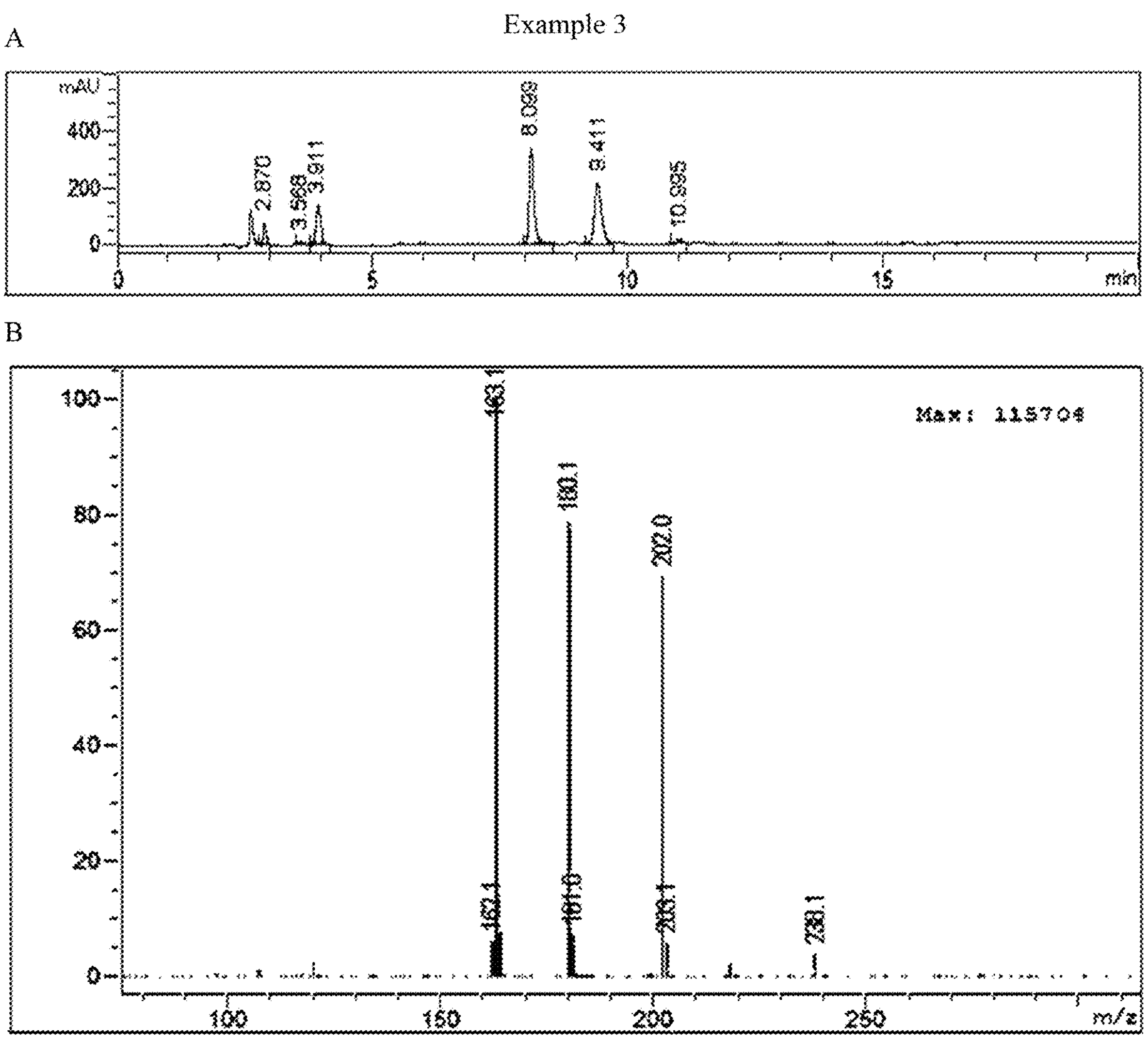
FIG. 9 is the Example 3 crystalline fine particle Form I of 3-AP forced degradation sample in Peroxide (3% H2O2) showing (A) the HPLC chromatogram at 220 nm with 5 degradants with the largest at RRT 0.87 peak (8.1 minutes) as 36.4% and (B) mass spectra of the major degradant peak at RRT 0.87 peak with [M+H]+ at 180.1, [M+Na]+ at 202.0, [M+H—NH3]+ at 163.1, and [M+ACH+NH3]+ at 238.1 m/z is Formula III: ##STR00003 ##: 3-amino-2-[(E)-(2-carbamothioylhydrazinylidene)methyl]-1-hydroxypyridin-1-ium.

Peroxide (3% $H_2O_2$) Degradation Sample: Based on the purity peak area at 220 nm, the control was 98.5% and the Peroxide (3% $H_2O_2$) sample was 1.2%. 3% H2O2 for 160 minutes reacted with 3-AP and formed 5 degradants with the largest at RRT 0.87 peak (8.1 minutes) as 36.4%. The HPLC chromatogram for the peroxide degradation sample at 220 nm is shown in FIG. 9A and MS spectra of the major degradant peak at RRT 0.87 (8.1 minutes) is shown in FIG. 9B. The proposed structure of the major degradant peak at RRT 0.87 with [M+H]+ at 180.1, [M+Na]+ at 202.0, [M+H−$NH_3$]+ at 163.1, and [M+ACH+$NH_3$]+ at 238.1 m/z is Formula III: ##STR00003 ##: 3-amino-2-[(E)-(2-carbamothioylhydrazinylidene)methyl]-1-hydroxypyridin-1-ium (FIG. 1).

Example 4—3-AP Excipient Compatibility Study. Excipient testing and compatibility studies were performed on the novel crystalline fine particle Form I of 3-AP. Excipient compatibility studies for binary blends (50:50 w/w) with the crystalline fine particle Form I of 3-AP sample mixed with (1) Lactose, Hydrous, NF, (2) Starch 1500, NF, (3) Sodium-lauryl-sulfate (SLS), NF, (4) Crospovidone, USP, (5) None (3-AP control), (6) Magnesium Stearate, NF, (7) Talc, USP, (8) Size 3 White Capsule Shell, and (9) Colloidal Silicon Dioxide, NF. Samples were analyzed by the HPLC assay described in Example 3. Samples stored at 40 degrees Celsius/75% RH and 60 degrees Celsius were tested by HPLC at 0 and 30 days (Table 7). Samples for HPLC analysis were filtered through a 0.45 micron PTFE filter for injection.

TABLE 7

| Sample | Timepoint | Condition | 3-AP % wt/wt |
|---|---|---|---|
| Lactose, Hydrous, NF | 0 | — | 100.0 |
| | 30 days | 40 C./75% RH | 98.6 |
| | 30 days | 60 C. | 102.3 |
| Starch 1500, NF | 0 | — | 100.2 |
| | 30 days | 40 C./75% RH | 99.5 |
| | 30 days | 60 C. | 100.9 |
| Sodium-lauryl-sulfate (SLS), NF | 0 | — | 99.9 |
| | 30 days | 40 C./75% RH | 99.6 |
| | 30 days | 60 C. | 99.7 |
| Crospovidone, USP | 0 | — | 99.3 |
| | 30 days | 40 C./75% RH | 97.7 |
| | 30 days | 60 C. | 99.7 |
| 3-AP control | 0 | — | 99.7 |
| | 30 days | 40 C./75% RH | 98.4 |
| | 30 days | 60 C. | 100.0 |
| Magnesium Stearate, NF | 0 | — | 98.9 |
| | 30 days | 40 C./75% RH | 100.6 |
| | 30 days | 60 C. | 100.3 |
| Talc, USP | 0 | — | 99.9 |
| | 30 days | 40 C./75% RH | 97.2 |
| | 30 days | 60 C. | 100.7 |
| Size 3 White Capsule Shell | 0 | — | 100.1 |
| | 30 days | 40 C./75% RH | 99.1 |
| | 30 days | 60 C. | 99.3 |
| Colloidal Silicon Dioxide, NF | 0 | — | 100.2 |
| | 30 days | 40 C./75% RH | 99.7 |
| | 30 days | 60 C. | 99.7 |

Overall, 3-AP was stable under all tested conditions with all excipients (Table 7). The 3-AP:talc (50:50) sample showed slight reduction (−2.8%) over the 30 day study at 40 degrees Celsius/75% RH but not at 60 degrees Celsius.

Example 5—Preparation of Crystalline 3-AP PDS. A mass of 5 g of crystalline fine particle Form I of 3-AP (Alchem Laboratories Corp.) and 15 g of Starch 1500, NF (Colorcon) was mixed in 50 mL tube. The powder was then ground into a fine powder using a mortar and pestle. Particles smaller than 500 microns were separated by sieving (30 mesh). The resulting white 25% powder was obtained with a yield of >90% crystalline 3-AP PDS powder, containing particles with a diameter less than 500 microns.

Example 6—Preparation of Immediate-Release Oral 3-AP Capsules. The immediate-release oral dosage form (gelatin capsules) containing the crystalline fine particle Form I of 3-AP particles prepared in Example 4 was dry mixed with additional Starch 1500, NF (Colorcon) and 0.4% magnesium stearate USP to achieve the correct capsule fill weight (300-400 mg) to achieve the desired dose. White gelatin #1 capsules were then filled with the mixture in a Torpac Profill 3700 machine to yield capsules containing 320 mg of 3-AP PDS with 50 mg 3-AP (15.6% of bulk PDS). Samples were taken to verify loading uniformity, content uniformity, assay, purity, and dissolution time. The validated HPLC assay AP3126R3 "Assay, Blend Uniformity, Content Uniformity and Related Substances by HPLC of 3-AP (Triapine) Capsules and Bulk Drug Product" was used with comparison to reference standard AL730-11.

The current Master Batch Record (MBR) is organized into four stages: (Stage 1 and 2) bulk blending of the drug product (DP), (Stage 3) capsule filling, and (Stage 4) check weight and bottle filling of the DP. The Stage 1 bulk blending steps involve mixing the API with Starch 1500. This mixture of Starch 1500 and API is sieved through a 500 μm mesh, Magnesium Stearate added, and then mixed in a planetary mixer for 5 minutes. A QC sample is tested for Triapine content in the bulk powder. In Stage 2 additional Starch 1500 is added, the mixture sieved again and then mixed in a planetary mixer for approximately 5 minutes. Another QC sample is tested for Triapine content in the bulk powder. In Stage 3 the bulk powder is encapsulated into size 1 white opaque capsules using a manual capsule filler. The target fill weight of these capsules is 320 mg. This is achieved after filling the capsules once then tamping, then filling the remaining amount of the bulk blend. Each sublot on the capsule filler fills 300 capsules, using approximately 90 to 100 g of blend. In Stage 4 filled capsules are weight sorted to confirm capsule weight specifications. All capsules are visually inspected for defects. The capsules are bulk packed into HDPE bottles with polypropylene screw caps. A seal is placed between the bottom of each cap and the neck of each bottle. Each bottle contains 30 capsules. The filled bottles are labeled, packed and stored at 25 degrees Celsius/60% relative humidity.

TABLE 8

| Capsules | Timepoint | Condition | Assay % wt/wt | Purity % a/a |
|---|---|---|---|---|
| NC1902001 (P83) | Time 0 | 25 C./60% RH | 96.8% | 99.78% |
| | 12 month | 25 C./60% RH | 97.1% | 99.78% |
| | 24 month | 25 C./60% RH | 95.9% | 99.79% |
| | 36 month | 25 C./60% RH | 93.4% | 99.76% |
| NC2011001 (P98) | Time 0 | 25 C./60% RH | 97.9% | 99.8% |
| | 12 month | 25 C./60% RH | 96.2% | 99.8% |
| | 24 month | 25 C./60% RH | 100.1% | 99.8% |
| NC2110003 (P107) | Time 0 | 25 C./60% RH | 102.8% | 99.8% |
| | 12 month | 25 C./60% RH | 96.2% | 99.8% |
| | 24 month | 25 C./60% RH | 100.1% | 99.7% |
| NP2206005 (P115) | Time 0 | 25 C./60% RH | 99.6% | 99.8% |
| | 12 month | 25 C./60% RH | 100.6% | 99.8% |
| | 24 month | 25 C./60% RH | 100.8% | 99.9% |
| | 36 month | 25 C./60% RH | 104.6% | 99.7% |
| NP2302002 (P118) | Time 0 | 25 C./60% RH | 95.7% | 99.8% |
| | 12 month | 25 C./60% RH | 100.2% | 99.5% |
| | 24 month | 25 C./60% RH | 99.2% | 99.6% |
| NP2305003 (P124) | Time 0 | 25 C./60% RH | 102.7% | 99.8% |
| | 12 month | 25 C./60% RH | 107.6% | 99.9% |
| | 24 month | 25 C./60% RH | 108.1% | 99.8% |
| NP2403002 (P137) | Time 0 | 25 C./60% RH | 95.7% | 99.8% |
| | 12 month | 25 C./60% RH | 109.9% | 99.3% |
| NP2410004 (P142) | Time 0 | 25 C./60% RH | 95.1% | 99.8% |
| | 12 month | 25 C./60% RH | Pending | Pending |

The stability (assay and purity) of eight lots of 3-AP Immediate-Release Oral Capsules, 50 mg Lots NC1902001, NC2011001, NC2110003, NP2206005, NP2302002, NP2305003, NP2403002, and NP2410004 have or are currently being monitored under stability protocols P83, P98, P107, P115, P118, P124, P137, and P142, respectively (Table 8). The stability of these eight cGMP lots support a 24 month shelf life at room temperature.

Example 7—Dissolution of Immediate-Release Oral 3-AP. Capsules from Example 6 were exposed to acidic (0.01N HCl) buffer using a USP apparatus II (paddle) for 30, 45, and 60 minutes to mimic the stomach environment. The validated HPLC assay AP3127R0 "Dissolution Testing of 3-AP (Triapine) 50 mg Capsules" was used in accordance with USP<711> with comparison to reference standard AL730-11. To demonstrate dissolution, more than 75% release of 3-AP in solution at 30 to 60 minutes in acidic buffer was tested using a USP dissolution apparatus and HPLC. All eight lots listed in Table 8 released more than 75% release of 3-AP in solution at 30 to 60 minutes in acidic buffer in accordance with USP<711> at all the tested time-points meeting required specifications.

What is claimed is:

1. A composition comprising a compound of Formula I:

Formula I

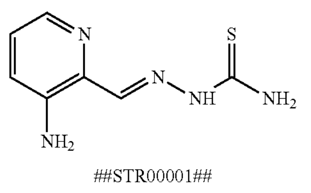

STR00001## wherein the compound of Formula I comprises a crystalline form of the compound of Formula I; wherein the crystalline form of the compound of Formula I is Form I characterized by an x-ray powder diffraction pattern comprising at least one peak selected from 10.4+/−0.3 degrees, 18.1+/−0.3 degrees, 19.7+/−0.3 degrees, 25.0+/−0.3 degrees, 25.5+/−0.3 degrees, 27.1+/−0.3 degrees, 30.9+/−0.3, 32.4+/−0.3 degrees and 50.0+/−0.3 degrees two theta.

2. The composition of claim 1, wherein the crystalline form of the compound of Formula I is Form I characterized by an x-ray powder diffraction pattern comprising at least one peak selected from 10.4+/−0.3 degrees, 18.1+/−0.3 degrees and 30.9+/−0.3 degrees two theta.

3. The composition of claim 1, wherein the crystalline form of the compound of Formula I is Form I characterized by an x-ray powder diffraction pattern substantially as set forth in FIG. 4A, FIG. 4B, FIG. 5A or FIG. 5B.

4. The composition of claim 1, wherein greater than 90% by weight of the compound of Formula I is the crystalline form of Form I characterized by an x-ray powder diffraction pattern comprising major peaks at 10.4+/−0.3 degrees, 18.1+/−0.3 degrees and 30.9+/−0.3 degrees two theta.

5. The composition of claim 1, wherein the compound of Formula I is the crystalline form of Form I characterized by an x-ray powder diffraction pattern comprising major peaks at 10.4+/−0.3 degrees, 18.1+/−0.3 degrees and 30.9+/−0.3 degrees two theta and is present in an amount ranging from about 0.01% to about 99.99% by mass of the composition.

6. The composition of claim 1, wherein the compound of Formula I has an average diameter of less than about 1 mm.

7. The composition of claim 1, wherein the compound of Formula I has an average diameter of less than about 500 μm.

8. The composition of claim 1, wherein the compound of Formula I is stable for at least 12 months at about 5 degrees Celsius or at about 25 degrees Celsius.

9. The composition of claim 1, wherein the composition further comprises:

(a) a compound of Formula II:

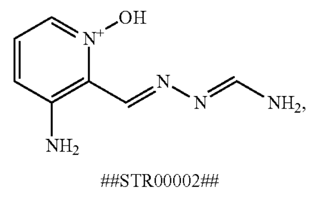 [SMILES: N/C=N/N=C/c1c(N)ccc[n+]1O]

STR00002##

(b) a compound of Formula III:

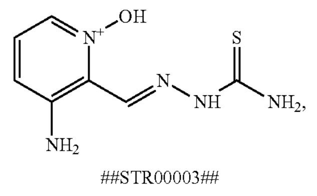 [SMILES: NC(=S)N/N=C/c1c(N)ccc[n+]1O]

STR00003## and/or (c) a compound of Formula IV:

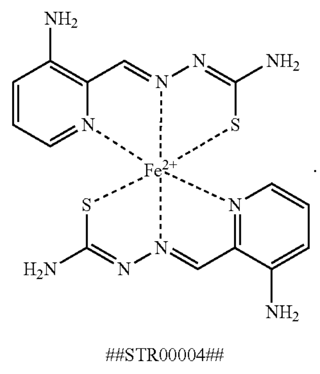

STR00004##

10. The composition of claim 9, wherein the composition comprises less than 0.5 weight % of the compound of Formula II, if present, less than 0.5 weight % of the compound of Formula III, if present, and less than 0.5 weight % of the compound of Formula IV, if present.

11. A particulate delivery system comprising a compound of Formula I:

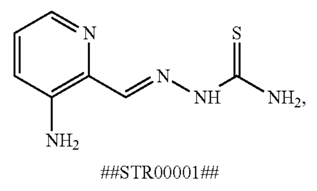 [SMILES: NC(=S)N/N=C/c1ncccc1N]

STR00001## and at least one pharmaceutically acceptable excipient, wherein the compound of Formula I comprises a crystalline form of the compound of Formula I; wherein the crystalline form of the compound of Formula I is Form I characterized by an x-ray powder diffraction pattern comprising at least one peak selected from 10.4+/−0.3 degrees, 18.1+/−0.3 degrees, 19.7+/−0.3 degrees, 25.0+/−0.3 degrees, 25.5+/−0.3 degrees, 27.1+/−0.3 degrees, 30.9+/−0.3, 32.4+/−0.3 degrees and 50.0+/−0.3 degrees two theta.

12. The particulate delivery system of claim 11, wherein the crystalline form of the compound of Formula I is Form I characterized by an x-ray powder diffraction pattern comprising at least one peak selected from 10.4+/−0.3 degrees, 18.1+/−0.3 degrees and 30.9+/−0.3 degrees two theta.

13. The particulate delivery system of claim 11, wherein the crystalline form of the compound of Formula I is Form I characterized by an x-ray powder diffraction pattern substantially as set forth in FIG. 4A or FIG. 4B.

14. The particulate delivery system of claim 11, wherein greater than 90% by weight of the compound of Formula I is the crystalline form of Form I characterized by an x-ray powder diffraction pattern comprising major peaks at 10.4+/−0.3 degrees, 18.1+/−0.3 degrees and 30.9+/−0.3 degrees two theta.

15. The particulate delivery system of claim 11, wherein the compound of Formula I is the crystalline form of Form I characterized by an x-ray powder diffraction pattern comprising major peaks at 10.4+/−0.3 degrees, 18.1+/−0.3 degrees and 30.9+/−0.3 degrees two theta and is present in an amount ranging from about 0.01% to about 99.99% by mass of the particulate delivery system.

16. The particulate delivery system of claim 11, wherein the compound of Formula I has an average diameter of less than about 1 mm.

17. The particulate delivery system of claim 11, wherein the compound of Formula I has an average diameter of less than about 500 μm.

18. The particulate delivery system of claim 11, wherein the at least one pharmaceutically acceptable excipient is a polymer.

19. The particulate delivery system of claim 18, wherein the polymer is chosen from starch, cellulose and polyethylene glycol.

20. The particulate delivery system of claim 11, wherein the particulate delivery system comprises 0.01 mg to 200 mg of the compound of Formula I.

21. The particulate delivery system of claim 11, wherein the compound of Formula I is stable for at least 12 months at about 5 degrees Celsius or at about 25 degrees Celsius.

22. The particulate delivery system of claim 11, wherein the particulate delivery system further comprises:

(a) a compound of Formula II:

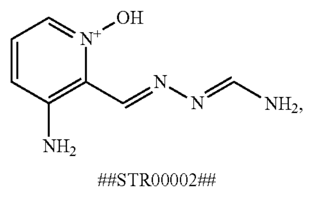 [SMILES: N/C=N/N=C/c1c(N)ccc[n+]1O]

STR00002##

(b) a compound of Formula III:

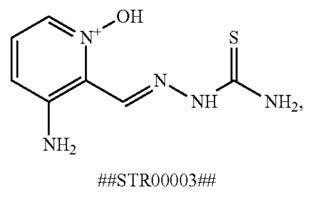 [SMILES: NC(=S)N/N=C/c1c(N)ccc[n+]1O]

STR00003## and/or (c) a compound of Formula IV:

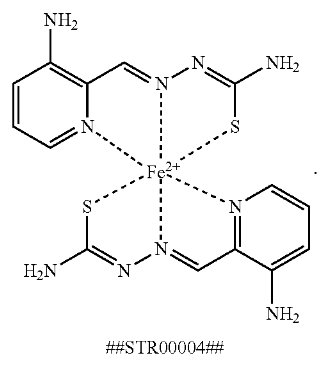

STR00004##

23. The particulate delivery system of claim 22, wherein the particulate delivery system comprises less than 0.5 weight % of the compound of Formula II, if present, less than 0.5 weight % of the compound of Formula III, if present, and less than 0.5 weight % of the compound of Formula IV, if present.

24. A method of making the particulate delivery system of claim 11, comprising:

blending the compound of Formula I together with the at least one pharmaceutically acceptable excipient to form a mixture;

processing said mixture to form coarse particles having an average diameter ranging from about 0.1 mm to about 5 mm; and grinding or milling said coarse particles to form particles having an average diameter less than about 500 μm.

25. A method of treating solid tumors and hematological malignancies, the method comprising administering an effective amount of the composition of claim 1 to a patient in need thereof.

26. The particulate delivery system of claim 11, wherein the crystalline form of the compound of Formula I is Form I is characterized by an x-ray powder diffraction pattern comprising at least one peak selected from 10.4+/−0.3 degrees, 18.1+/−0.3 degrees, 30.9+/−0.3, 25.0+/−0.3 degrees, 25.5+/−0.3 degrees and 27.1+/−0.3 degrees, 19.7+/−0.3 degrees, 32.4+/−0.3 degrees and 50.0+/−0.3 degrees two theta, wherein greater than 90% by weight of the compound of Formula I is Form I, wherein the compound of Formula I has an average diameter of less than about 500 μm, wherein the compound of Formula I is stable for at least 12 months at 5 degrees Celsius or at 25 degrees Celsius, and wherein the particulate delivery system is formulated for oral delivery.

27. A process for manufacturing a crystalline form of a compound of Formula I:

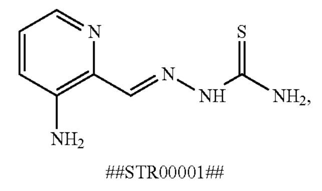 [SMILES: NC(=S)N/N=C/c1ncccc1N]

STR00001## comprising the steps of:

(a) Boc protection of 3-(tert-butoxycarbonylamino)-2-bromopyridine with a 1M solution of sodium bis(trimethylsilyl) amide (NaHMDS) in THF (2.1 equiv.) added dropwise to a solution of 3-amino-2-bromopyridine (1 equiv.) and di-t-butylcarbonate in THF at 0 degrees Celsius, (b) synthesis of 3-(N-tert-butoxycarbonylamino)-2-pyridinecarboxaldehyde by treatment of the tert-boc protected 3-amino-2-bromopyridine with n-BuLi in anhydrous THF resulting in the lithiated species, which was further reacted with N-formylpiperidine at low temperature (−65 to −70 degrees Celsius), and (c) condensation of 3-(N-tert-butoxycarbonylamino)-2-pyridinecarboxaldehyde with thiosemicarbazide in ethanol and water in the presence of concentrated HCl and deprotection to prepare 3-AP hydrochloride, which is converted into the free base by basification with sodium bicarbonate solution, cooled to room temperature overnight followed by 1-5 degrees Celsius for 1 hour for crystallization, washed with cold water, ethanol, and diethyl ether, and then vacuum dried to obtain coarse particles, whereas the crystalline form of a compound of Formula I is Form I, and wherein the crystalline form of a compound of Formula I is obtained by grinding the coarse particles or sieving.

28. The process of claim 27, further comprising an input 3-AP hydrochloride and addition of sodium bicarbonate solution to provide crystalline 3-AP solid and a mother liquor followed by separation and drying, wherein greater than 90% by weight of the compound of Formula I obtained from the process is the crystalline form of the compound of Formula I.

* * * * *